United States Patent
Scarborough et al.

(10) Patent No.: US 6,211,154 B1
(45) Date of Patent: *Apr. 3, 2001

(54) KETOHETEROCYCLIC INHIBITORS OF FACTOR XA

(75) Inventors: Robert M. Scarborough, Belmont; Charles K. Marlowe, Redwood City; Bing-Yan Zhu, Foster City, all of CA (US)

(73) Assignee: COR Therapeutics, Inc., South San Francisco, CA (US)

( * ) Notice: This patent issued on a continued prosecution application filed under 37 CFR 1.53(d), and is subject to the twenty year patent term provisions of 35 U.S.C. 154(a)(2).

Subject to any disclaimer, the term of this patent is extended or adjusted under 35 U.S.C. 154(b) by 0 days.

This patent is subject to a terminal disclaimer.

(21) Appl. No.: 08/480,491

(22) Filed: Jun. 7, 1995

(51) Int. Cl.⁷ .............................. C07K 5/08; A61K 38/03
(52) U.S. Cl. ........................ 514/18; 530/331; 544/224; 546/246; 548/146
(58) Field of Search .................. 546/246; 514/18; 530/331; 544/224; 548/146

(56) References Cited

U.S. PATENT DOCUMENTS

| | | | |
|---|---|---|---|
| 3,867,364 | 2/1975 | Umezawa | 260/112.5 |
| 4,797,472 | * 1/1989 | Gustavsson et al. | 530/331 |
| 5,153,176 | * 10/1992 | Abe et al. | 514/18 |
| 5,523,308 | 6/1996 | Costanzo | 514/317 |

FOREIGN PATENT DOCUMENTS

| | | |
|---|---|---|
| 0 195 212 A3 | 9/1986 | (EP) . |
| 0 275 101 A3 | 7/1988 | (EP) . |
| 0 364 344 A3 | 4/1990 | (EP) . |
| 0 410 411 A2 | 1/1991 | (EP) . |
| 0 417 721 A2 | 3/1991 | (EP) . |
| 648780 | 4/1995 | (EP) . |
| 93/14779 | * 8/1993 | (WO) . |
| 94/25051 | * 11/1994 | (WO) . |
| WO 95/09634 | 4/1995 | (WO) . |
| WO 96/19493 | 6/1996 | (WO) . |

OTHER PUBLICATIONS

Dayhoff et al., Atlas of Protein Sequence and Structure (1972) vol. 5 pp. 89–99.*
Ohta et al., "Interaction of Antistasin–related Peptides with Factor Xa: Identification of a Core Inhibitory Sequence", Thrombosis and Haemostasis 72(6)825–830 (1994).
Silverman, The Organic Chemistry of Drug Design and Drug Action, pp. 352–401, 1992.*
Bundgard, H. "Design of Prodrugs", pp. 7–9, 21–24, 1985.*
Spatola, "Chemistry and Biochemistry of Amino Acids and Proteins" B. Weinstein Ed. pp. 267–355, 1983.*
H. Hruby, "Life Sciences", vol. 31, pp. 189–199, 1982.*
Edwards & Wolanin et al., J. Med. Chem. vol. 38, pp. 76–85, 1995.*
Edwards & Meyer et al., J. Am. Chem. Soc. vol. 114 No. 5, pp. 1854–1863, 1992.*
Tsutsumi et al., J. Med. Chem. vol. 37, No. 21, pp. 3492–3502, 1994.*
Claeson, Blood Coagulation and Fibrinolysis, vol. 5 pp. 411–436, 1994.*

* cited by examiner

*Primary Examiner*—Bennett Celsa
(74) *Attorney, Agent, or Firm*—Cooley Godward LLP

(57) ABSTRACT

Novel compounds, their salts and compositions related thereto having activity against mammalian factor Xa are disclosed. The compounds are useful in vitro or in vivo for preventing or treating coagulation disorders.

45 Claims, No Drawings

KETOHETEROCYCLIC INHIBITORS OF FACTOR XA

FIELD OF THE INVENTION

This invention relates to novel ketoheterocyclic-containing compounds which are potent and highly selective inhibitors of isolated factor Xa or when assembled in the prothrombinase complex. In another aspect, the present invention relates to novel peptide and peptide mimetic analogs, their pharmaceutically acceptable salts, and pharmaceutically acceptable compositions thereof which are useful as potent and specific inhibitors of blood coagulation in mammals. In yet another aspect, the invention relates to methods for using these inhibitors as therapeutic agents for disease states in mammals characterized by coagulation disorders.

BACKGROUND OF THE INVENTION

Hemostasis, the control of bleeding, occurs by surgical means, or by the physiological properties of vasoconstriction and coagulation. This invention is particularly concerned with blood coagulation and ways in which it assists in maintaining the integrity of mammalian circulation after injury, inflammation, disease, congenital defect, dysfunction or other disruption. Under normal hemostatic circumstances, the body maintains an acute balance of clot formation and clot removal (fibrinolysis). The blood coagulation cascade involves the conversion of a variety of inactive enzymes (zymogens) into active enzymes which ultimately convert the soluble plasma protein fibrinogen into an insoluble matrix of highly cross-linked fibrin, Davie, E. J. et al., "The Coagulation Cascade: Initiation, Maintenance and Regulation", Biochemistry, 30, 10363–10370 (1991). These plasma glycoprotein zymogens include Factor XII, Factor XI, Factor IX, Factor X, Factor VII, and prothrombin. Blood coagulation follows either the intrinsic pathway, where all of the protein components are present in blood, or the extrinsic pathway, where the cell-membrane protein tissue factor plays a critical role. Clot formation occurs when fibrinogen is cleaved by thrombin to form fibrin. Blood clots are composed of activated platelets and fibrin.

Blood platelets which adhere to damaged blood vessels are activated and incorporated into the clot and thus play a major role in the initial formation and stabilization of hemostatic "plugs". In certain diseases of the cardiovascular system, deviations from normal hemostasis push the balance of clot formation and clot dissolution towards life-threatening thrombus formation when thrombi occlude blood flow in coronary vessels (myocardial infarctions) or limb and pulmonary veins (venous thrombosis). Although platelets and blood coagulation are both involved in thrombus formation, certain components of the coagulation cascade are primarily responsible for the amplification or acceleration of the processes involved in platelet aggregation and fibrin deposition.

Thrombin is a key enzyme in the coagulation cascade as well as in hemostasis. Thrombin plays a central role in thrombosis through its ability to catalyze the conversion of fibrinogen into fibrin and through its potent platelet activation activity. Under normal circumstances, thrombin can also play an anticoagulant role in hemostasis through its ability to convert protein C into activated protein C (aPC) in a thrombomodulin-dependent manner. However, in atherosclerotic arteries these thrombin activities can initiate the formation of a thrombus, which is a major factor in pathogenesis of vasoocclusive conditions such as myocardial infarction, unstable angina, nonhemorrhagic stroke and reocclusion of coronary arteries after angioplasty or thrombolytic therapy. Thrombin is also a potent inducer of smooth muscle cell proliferation and may therefore be involved in a variety of proliferative responses such as restenosis after angioplasty and graft induced atherosclerosis. In addition, thrombin is chemotactic for leukocytes and may therefore play a role in inflammation. (Hoover, R. J., et al. Cell, 14, 423 (1978); Etingin, O. R., et al., Cell, 61, 657 (1990). These observations indicate that inhibition of thrombin formation or inhibition of thrombin itself may be effective in preventing or treating thrombosis, limiting restenosis and controlling inflammation.

Direct or indirect inhibition of thrombin activity has been the focus of a variety of recent anticoagulant strategies as reviewed by Claeson, G., "Synthetic Peptides and Peptidomimetics as Substrates and Inhibitors of Thrombin and Other Proteases in the Blood Coagulation System", Blood Coag. Fibrinol. 5, 411–436 (1994). Several classes of anticoagulants currently used in the clinic directly or indirectly affect thrombin (i.e. heparins, low-molecular weight heparins, heparin-like compounds and coumarins).

The formation of thrombin is the result of the proteolytic cleavage of its precursor prothrombin at the Arg—Thr linkage at positions 271–272 and the Arg—Ile linkage at positions 320–321. This activation is catalyzed by the prothrombinase complex, which is assembled on the membrane surfaces of platelets, monocytes, and endothelial cells. The complex consists of Factor Xa (a serine protease), Factor Va (a cofactor), calcium ions and the acidic phospholipid surface. Factor Xa is the activated form of its precursor, Factor X, which is secreted by the liver as a 58 kd precursor and is converted to the active form, Factor Xa, in both the extrinsic and intrinsic blood coagulation pathways. Factor X is a member of the calcium ion binding, gamma carboxyglutamyl (Gla)-containing, vitamin K dependent, blood coagulation glycoprotein family, which also includes Factors VII and IX, prothrombin, protein C and protein S (Furie, B., et al., Cell, 53, 505 (1988)). The activity of Factor Xa in effecting the conversion of prothrombin to thrombin is dependent on its inclusion in the prothrombinase complex.

The prothrombinase complex converts the zymogen prothrombin into the active procoagulant thrombin. It is therefore understood that Factor Xa catalyzes the next-to-last step in the blood coagulation cascade, namely the formation of the serine protease thrombin. In turn, thrombin then acts to cleave soluble fibrinogen in the plasma to form insoluble fibrin.

The location of the prothrombinase complex at the convergence of the intrinsic and extrinsic coagulation pathways, and the resulting significant amplification of thrombin generation (several hundred-thousand fold faster in effecting the conversion of prothrombin to thrombin than Factor Xa in soluble form) mediated by the complex at a limited number of targeted catalytic units present at vascular lesion sites, suggests that inhibition of thrombin generation is a desirable method to block uncontrolled procoagulant activity. It has been suggested that compounds which selectively inhibit factor Xa may be useful as in vitro diagnostic agents, or for therapeutic administration in certain thrombotic disorders, see e.g., WO 94/13693. Unlike thrombin, which acts on a variety of protein substrates as well as at a specific receptor, factor Xa appears to have a single physiologic substrate, namely prothrombin.

Plasma contains an endogenous inhibitor of both the factor VIIa-tissue factor (TF) complex and factor Xa called tissue factor pathway inhibitor (TFPI). TFPI is a Kunitz-type protease inhibitor with three tandem Kunitz domains. TFPI inhibits the TF/fVIIa complex in a two-step mechanism which includes the initial interaction of the second Kunitz domain of TFPI with the active site of factor Xa, thereby inhibiting the proteolytic activity of factor Xa. The second step involves the inhibition of the TF/fVIIa complex by formation of a quaternary complex TF/fVII/TFPI/fXa as described by Girard, T. J. et al., "Functional Significance of the Kunitz-type Inhibitory Domains of Lipoprotein-associated Coagulation Inhibitor", Nature, 338, 518–520 (1989).

Polypeptides derived from hematophagous organisms have been reported which are highly potent and specific inhibitors of factor Xa. U.S. Pat. No. 4,588,587 describes anticoagulant activity in the saliva of the Mexican leech, Haementeria officinalis. A principal component of this saliva was shown to be the polypeptide factor Xa inhibitor, antistasin (ATS), by Nutt, E. et al., "The Amino Acid Sequence of Antistasin, a Potent Inhibitor of Factor Xa Reveals a Repeated Internal Structure", J. Biol. Chem., 263, 10162–10167 (1988).

Another potent and highly specific inhibitor of Factor Xa, called tick anticoagulant peptide (TAP), has been isolated from the whole body extract of the soft tick *Omithidoros moubata*, as reported by Waxman, L., et al., "Tick Anticoagulant Peptide (TAP) is a Novel Inhibitor of Blood Coagulation Factor Xa" Science, 248, 593–596 (1990).

Other polypeptide type inhibitors of factor Xa have been reported including the following: Condra, C. et al., "Isolation and Structural Characterization of a Potent Inhibitor of Coagulation Factor Xa from the Leech *Haementeria ghilianii*", Thromb. Haemost., 61, 437–441 (1989); Blankenship, D. T. et al., "Amino Acid Sequence of Ghilanten: Anti-coagulant-antimetastatic Principle of the South American Leech, *Haementeria ghilianii*", Biochem. Biophys. Res. Commun. 166, 1384–1389 (1990); Brankamp, R. G. et al., "Ghilantens: Anticoagulants, Antimetastatic Proteins from the South American Leech *Haementeria ghilianii*", J. Lab. Clin. Med., 115, 89–97 (1990); Jacobs, J. W. et al., "Isolation and Characterization of a Coagulation Factor Xa Inhibitor from Black Fly Salivary Glands", Thromb. Haemost., 64, 235–238 (1990); Rigbi, M. et al., "Bovine Factor Xa Inhibiting Factor and Pharmaceutical Compositions Containing the Same", European Patent Application, 352,903; Cox, A. C., "Coagulation Factor X Inhibitor From the Hundred-pace Snake *Deinagkistrodon acutus*, venom", Toxicon, 31, 1445–1457 (1993); Cappello, M. et al., "Ancylostoma Factor Xa Inhibitor: Partial Purification and its Identification as a Major Hookworm-derived Anticoagulant In Vitro", J. Infect. Dis., 167,1474–1477 (1993); Seymour, J. L. et. al., "Ecotin is a Potent Anticoagulant and Reversible Tight-binding Inhibitor of Factor Xa", Biochemistry 33, 3949–3958 (1994).

Factor Xa inhibitory compounds which are not large polypeptide-type inhibitors have also been reported including: Tidwell, R. R. et al., "Strategies for Anticoagulation With Synthetic Protease Inhibitors. Xa Inhibitors Versus Thrombin Inhibitors", Thromb. Res., 19, 339–349 (1980); Turner, A. D. et al., "p-Amidino Esters as Irreversible Inhibitors of Factor IXa and Xa and Thrombin", Biochemistry, 25, 4929–4935 (1986); Hitomi, Y. et al., "Inhibitory Effect of New Synthetic Protease Inhibitor (FUT-175) on the Coagulation System", Haemostasis, 15, 164–168 (1985); Sturzebecher, J. et al., "Synthetic Inhibitors of Bovine Factor Xa and Thrombin. Comparison of Their Anticoagulant Efficiency", Thromb. Res., 54 245–252 (1989); Kam, C. M. et al., "Mechanism Based Isocoumarin Inhibitors for Trypsin and Blood Coagulation Serine Proteases: New Anticoagulants", Biochemistry, 27, 2547–2557 (1988); Hauptmann, J. et al., "Comparison of the Anticoagulant and Antithrombotic Effects of Synthetic Thrombin and Factor Xa Inhibitors", Thromb. Haemost., X, 220–223 (1990); Miyadera, A. et al., Japanese Patent Application JP 6327488; Nagahara, T. et al., "Dibasic (Amidinoaryl) propanoic Acid Derivatives as Novel Blood Coagulation Factor Xa Inhibitors", J. Med. Chem., Z, 1200–1207 (1994); Vlasuk, G. P. et al., "Inhibitors of Thrombosis", WO 93/15756; and Brunck, T. K. et al., "Novel Inhibitors of Factor Xa", WO 94/13693.

A number of inhibitors of trypsin-like enzymes (such as trypsin, enterokinase, thrombin, kallikrein, plasmin, urokinase, plasminogen activators and the like) have been the subject of disclosures. For example, Austen et al., U.S. Pat. No. 4,593,018 describes oligopeptide aldehydes which are specific inhibitors of enterokinase; Abe et al., U.S. Pat. No. 5,153,176 describes tripeptide aldehydes which have inhibitory activity against multiple serine proteases such as plasmin, thrombin, trypsin, kallikrein, factor Xa, urokinase, etc.; Brunck et al., European Publication WO 93/14779 describes substituted tripeptide aldehydes that are specific inhibitors of trypsin; U.S. Pat. No. 4,316,889, U.S. Pat. No. 4,399,065, U.S. Pat. No. 4,478,745 all disclose arginine aldehyde inhibitors of thrombin; Balasubramanian et al., U.S. Pat. No. 5,380,713 describes di and tripeptide aldehydes which are useful for anti-trypsin and anti-thrombin activity; Webb et al., U.S. Pat. No. 5,371,072 describes tripeptide alpha-keto-amide derivatives as inhibitors of thrombosis and thrombin; Gesellchen et al., European Patent Publications 0479489A2 and 0643073 A, describe tripeptide thrombin inhibitors; Veber et al., European Publication WO 94/25051 describes 4-cyclohexylamine derivatives which selectively inhibit thrombin over other trypsin-like enzymes; Tapparelli et al., J. Biol. Chem. 268, 4734–4741 (1993) describe selective peptide boronic acid derivatives as inhibitors of thrombin.

Alternatively, agents which inhibit the vitamin K-dependent carboxylase enzyme, such as coumarn, have been used to treat coagulation disorders.

There exists a need for effective therapeutic agents for the regulation of hemostasis, and for the prevention and treatment of thrombus formation and other pathological processes in the vasculature induced by thrombin such as restenosis and inflammation.

SUMMARY OF THE INVENTION

The present invention relates to novel peptide and peptide mimetic analogs, their pharmaceutically acceptable isomers, salts, hydrates, solvates and prodrug derivatives, and pharmaceutically acceptable compositions thereof which have particular biological properties and are useful as potent and specific inhibitors of blood coagulation in mammals. In another aspect, the invention relates to methods of using these inhibitors as diagnostic reagents or as therapeutic agents for disease states in mammals which have coagulation disorders, such as in the treatment or prevention of any thrombotically mediated acute coronary or cerebrovascular syndrome, any thrombotic syndrome occurring in the venous system, any coagulopathy, and any thrombotic complications associated with extracorporeal circulation or instrumentation, and for the inhibition of coagulation in biological samples.

In certain embodiments, this invention relates to novel arginine and arginine mimetic-containing compounds which are potent and highly selective inhibitors of isolated factor Xa when assembled in the prothrombinase complex. These compounds show selectivity for factor Xa versus other proteases of the coagulation cascade (e.g. thrombin, etc.) or the fibrinolytic cascade, and are useful as diagnostic reagents as well as antithrombotic agents.

In preferred embodiments, the present invention provides compounds of the formula:

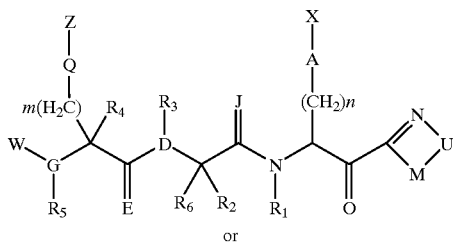

or

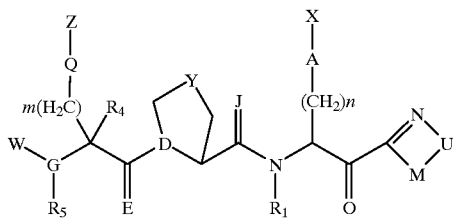

wherein:

m=0,1,2,3,4;

n=0,1,2,3,4;

Y=NH, S, O, CH$_2$, CH—OH, CH$_2$CH$_2$, C=O;

A=piperdinyl, pyrrolidinyl, cyclopropyl, cyclobutyl, cyclopentyl, cyclohexyl, phenyl, C$_{3-6}$heteroaryl, or is absent;

R$_1$=H or C$_{1-3}$alkyl;

J=O or H$_2$;

R$_2$=H or C$_{1-3}$alkyl;

D=N, CH, NCH$_2$, NCH$_2$CH$_2$, CHCH$_2$;

R$_3$=H or C$_{1-3}$alkyl;

E=O or H$_2$;

R$_4$=H or CH$_3$;

M=NH, N—CH$_3$, O, S, SO, SO$_2$ or CH$_2$ or is absent;

Q=piperdinyl, pyrrolidinyl, C$_{3-8}$ cycloalkyl, phenyl, substituted phenyl, naphthyl, pyridyl, or is absent;

G=N, CH, or H;

R$_5$=H or C$_{1-3}$ alkyl or is absent if G is H;

R$_6$=H or CH$_3$;

U=is selected from the group consisting of

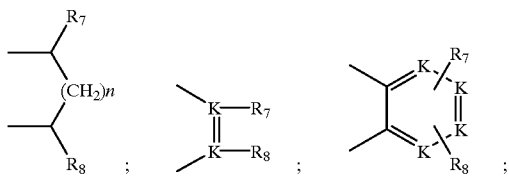

where n=0–4; R$_7$ and R$_8$ are independently selected from a group consisting of H, C$_{1-10}$alkyl, aryl, arylalkyl, halogen, nitro, an amino group of formula —NR$_9$R$_{10}$, an acylamino group of formula —NHCOR$_{11}$, hydroxy, an acyloxy group of formula —OCOR$_{12}$, C$_{1-4}$alkyloxy, C$_{1-4}$alkyl, trifluoromethyl, carboxy, cyano, phenyl, an aromatic heterocyclic group, C$_{1-4}$alkyloxycarbonyl, an aminocarbonyl group of formula CONR$_{13}$R$_{14}$, sulfo, sulfonamido of formula SO$_2$NR$_{15}$R$_{16}$ and C$_{1-6}$ hydroxyalkyl, wherein R$_9$,R$_{10}$, R$_{11}$, R$_{12}$, R$_{13}$, R$_{14}$, R$_{15}$, R$_{16}$ are the same or different and =H, C$_{1-6}$ alkyl, C$_{1-3}$arylalkyl or aryl; and if M is absent:

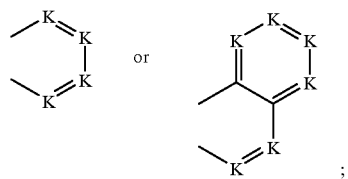

K=C or N;

W=H, arylacyl, heteroarylacyl, arylC$_{1-3}$alkylsulfonyl, arylsulfonyl, substituted arylsulfonyl, arylC$_{1-4}$alkenylsulfonyl, C$_{1-8}$ alkylsulfonyl, heteroarylC$_{1-3}$alkylsulfonyl, heteroarylsulfonyl, aryloxycarbonyl, C$_{1-6}$ alkyloxycarbonyl, arylC$_{1-3}$alkyloxycarbonyl, arylaminocarbonyl, C$_{1-6}$alkylaminocarbonyl, arylC$_{1-3}$alkylaminocarbonyl, HOOC—C$_0$— $_3$alkylcarbonyl, or is absent if G is H;

X=NR'R'', NH—C(NR'R'')=NH, NH—C(NHR')=NR'', NH—C(R')=NR'', S— C(NR'R'')=NH, S—C(NHR')=NR'', C(NR'R'')=NH, C(NHR')=NR'', or CR'=NR''; where: R',R'' are the same or different and =H, C$_{1-6}$alkyl, C$_{1-3}$arylalkyl, aryl or where R'R'' forms a cyclic ring containing (CH$_2$)$_p$ where p=2–5;

Z=NR'R'', NH—C(NR'R'')=NH, NH—C(NHR')=NR'', NH—C(R')=NR'', S— C(NR'R'')=NH, S—C(NHR') =NR'', C(NR'R'')=NH, C(NHR')=NR'', or CR'=NR''; where: R',R'' are the same or different and =H, C$_{1-6}$alkyl, C$_{1-3}$arylalkyl, aryl or where R'R'' forms a cyclic ring containing (CH$_2$)$_p$ where p=2–5;

and all pharmaceutically acceptable isomers, salts, hydrates, solvates and prodrug derivatives thereof.

In certain aspects of this invention, compounds are provided which are useful as diagnostic reagents. In another aspect, the present invention includes pharmaceutical compositions comprising a pharmaceutically effective amount of the compounds of this invention and a pharmaceutically acceptable carrier. In yet another aspect, the present invention includes methods comprising using the above compounds and pharmaceutical compositions for preventing or treating disease states characterized by disorders of the blood coagulation process in mammals, or for preventing coagulation in stored blood products and samples. Optionally, the methods of this invention comprise administering the pharmaceutical composition in combination with an additional therapeutic agent such as an antithrombotic and/or a thrombolytic agent and/or an anticoagulant.

The preferred compounds also include their pharmaceutically acceptable isomers, hydrates, solvates, salts and prodrug derivatives.

DETAILED DESCRIPTION OF THE INVENTION

Definitions

In accordance with the present invention and as used herein, the following terms are defined with the following meanings, unless explicitly stated otherwise.

The term "alkenyl" refers to a trivalent straight chain or branched chain unsaturated aliphatic radical.

The term "alkyl" refers to saturated aliphatic groups including straight-chain, branched-chain and cyclic groups having the number of carbon atoms specified, or if no number is specified, having up to 12 carbon atoms. The term "cycloalkyl" as used herein refers to a mono-, bi-, or tricyclic aliphatic ring having 3 to 14 carbon atoms and preferably 3 to 7 carbon atoms.

The term "aryl" refers to an unsubstituted or substituted aromatic ring, substituted with one, two or three substituents selected from loweralkoxy, loweralkyl, loweralkylamino, hydroxy, halogen, cyano, hydroxyl, mercapto, nitro, thioalkoxy, carboxaldehyde, carboxyl, carboalkoxy and carboxamide, including but not limited to carboyclic aryl, heterocyclic aryl, and biaryl groups and the like, all of which may be optionally substituted. Preferred aryl groups include phenyl, halophenyl, loweralkylphenyl, napthyl, biphenyl, phenanthrenyl, naphthacenyl, and aromatic heterocyclics. The term "heteroaryl" as used herein refers to any aryl group, containing from one to four heteroatoms, selected from the group consisting of nitrogen, oxygen and sulfur.

The term "arylalkyl" refers to one, two, or three aryl groups having the number of carbon atoms designated, appended to an alkyl group having the number of carbon atoms designated. Suitable arylalkyl groups include, but are not limited to, benzyl, picolyl, naphthylmethyl, phenethyl, benzyhydryl, trityl, and the like, all of which may be optionally substituted.

The terms "halo" or "halogen" as used herein refer to Cl, Br, F or l substituents.

The term "methylene" refers to —CH$_2$—.

The term "pharmaceutically acceptable salts" includes salts of compounds derived from the combination of a compound and an organic or inorganic acid. These compounds are useful in both free base and salt form. In practice, the use of the salt form amounts to use of the base form; both acid and base addition salts are within the scope of the present invention.

"Pharmaceutically acceptable acid addition salt" refers to those salts which retain the biological effectiveness and properties of the free bases and which are not biologically or otherwise undesirable, formed with inorganic acids such as hydrochloric acid, hydrobromic acid, sulfuric acid, nitric acid, phosphoric acid and the like, and organic acids such as acetic acid, propionic acid, glycolic acid, pyruvic acid, oxalic acid, maleic acid, malonic acid, succinic acid, fumaric acid, tartaric acid, citric acid, benzoic acid, cinnamic acid, mandelic acid, methanesulfonic acid, ethanesulfonic acid, p-toluenesulfonic acid, salicyclic acid and the like.

"Pharmaceutically acceptable base addition salts" include those derived from inorganic bases such as sodium, potassium, lithium, ammonium, calcium, magnesium, iron, zinc, copper, manganese, aluminum salts and the like. Particularly preferred are the ammonium, potassium, sodium, calcium and magnesium salts. Salts derived from pharmaceutically acceptable organic nontoxic bases include salts of primary, secondary, and tertiary amines, substituted amines including naturally occurring substituted amines, cyclic amines and basic ion exchange resins, such as isopropylamine, trimethylamine, diethylamine, triethylamine, tripropylamine, ethanolamine, 2-diethylaminoethanol, trimethamine, dicyclohexylamine, lysine, arginine, histidine, caffeine, procaine, hydrabamine, choline, betaine, ethylenediamine, glucosamine, methylglucamine, theobromine, purines, piperizine, piperidine, N-ethylpiperidine, polyamine resins and the like. Particularly preferred organic nontoxic bases are isopropylamine, diethylamine, ethanolamine, trimethamine, dicyclohexylamine, choline, and caffeine.

"Biological property" for the purposes herein means an in vivo effector or antigenic function or activity that is directly or indirectly performed by a compound of this invention. Effector functions include receptor or ligand binding, any enzyme activity or enzyme modulatory activity, any carrier binding activity, any hormonal activity, any activity in promoting or inhibiting adhesion of cells to an extracellular matrix or cell surface molecules, or any structural role. Antigenic functions include possession of an epitope or antigenic site that is capable of reacting with antibodies raised against it.

The nomenclature used to describe the peptide compounds of the invention follows the conventional practice where the N-terminal amino group is assumed to be to the left and the carboxy group to the right of each amino acid residue in the peptide. In the formulas representing selected specific embodiments of the present invention, the amino- and carboxy-terminal groups, although often not specifically shown, will be understood to be in the form they would assume at physiological pH values, unless otherwise specified. Thus, the N-terminal H$^+_2$ and C-terminal O$^-$ at physiological pH are understood to be present though not necessarily specified and shown, either in specific examples or in generic formulas. Free functional groups on the side chains of the amino acid residues can also be modified by amidation, acylation or other substitution, which can, for example, change the solubility of the compounds without affecting their activity.

In the peptides described herein, each gene-encoded residue, where appropriate, is represented by a single letter designation, corresponding to the trivial name of the amino acid, in accordance with the following conventional list

| Amino Acid | One-Letter Symbol | Three-letter Symbol |
| --- | --- | --- |
| Alanine | A | Ala |
| Arginine | R | Arg |
| Asparagine | N | Asn |
| Aspartic acid | D | Asp |
| Cysteine | C | Cys |
| Glutamine | Q | Gln |
| Glutamic acid | E | Glu |
| Glycine | G | Gly |
| Histidine | H | His |
| Isoleucine | I | Ile |
| Leucine | L | Leu |
| Lysine | K | Lys |
| Methionine | M | Met |
| Phenylalanine | F | Phe |
| Proline | P | Pro |
| Serine | S | Ser |
| Threonine | T | Thr |
| Tryptophan | W | Trp |
| Tyrosine | Y | Tyr |
| Valine | V | Val |

In addition, the following abbreviations are used in this application:

"Ala" refers to L-Alanine.

"D-Ala" refers to D-Alanine.

"Arg" refers to L-Arginine.

"D-Arg" refers to D-Arginine.

"Bn" refers to benzyl.

"t-Boc" refers to t-butoxycarbonyl.

"BOP" refers to benzotriazol-1-yloxy-tris-(dimethylamino)phosphonium hexafluorophosphate.

"Cbz" refers to benzyloxycarbonyl.

"DCM" refers to dichloromethane.

"DIEA" refers to diisopropylethylamine.

"DMF" refers to N,N-dimethylformamide.

"EDC" refers to ethyl-3-(3-dimethylamino)-propyl carbodiimide.HCL

"EtOAc" refers to ethyl acetate.

"Gly" refers to glycine.

"HOSu" refers to N-hydroxysuccinimide.

"D-Lys" refers to D-Lysine.

"MeOH" refers to methanol.

"MeSEt" refers to methyl ethyl sulfide.
"NaOAc" refers to sodium acetate.
"Ph" refers to phenyl.
"D-Pro" refers to D-proline.
"Pro" refers to L-proline.
"TEA" refers to triethylamine.
"TFA" refers to trifluoroacetic acid.
"THF" refers to tetrahydrofuran.
"Tos" refers to p-toluenesulfonyl.

The amino acids not encoded genetically are abbreviated as described above or have the meanings commonly accepted in the field.

In the compounds of this invention, carbon atoms bonded to four non-identical substituents are asymmetric. Accordingly, the compounds may exist as diastereoisomers, enantiomers or mixtures thereof. The syntheses described herein may employ racemates, enantiomers or diastereomers as starting materials or intermediates. Diastereomeric products resulting from such syntheses may be separated by chromatographic or crystallization methods, or by other methods known in the art. Likewise, enantiomeric product mixtures may be separated using the same techniques or by other methods known in the art. Each of the asymmetric carbon atoms, when present in the compounds of this invention, may be in one of two configurations (R or S) and both are within the scope of the present invention. In certain specified preferred embodiments of the compounds shown in the present application, the L-form of any amino acid residue having an optical isomer is intended unless the D-form is expressly indicated. In the processes described above, the final products may, in some cases, contain a small amount of the products having D or L-form residues, however these products do not affect their therapeutic or diagnostic application.

The compounds of the invention are peptides or compounds which contain amino acid subunits which are partially defined in terms of amino acid residues of designated classes. Amino acid residues can be generally grouped into four major subclasses as follows:

Acidic: The residue has a negative charge due to loss of H ion at physiological pH and the residue is attracted by aqueous solution.

Basic: The residue has a positive charge due to association with H ion at physiological pH and the residue is attracted by aqueous solution.

Neutra/nonpolar: The residues are not charged at physiological pH and the residue is repelled by aqueous solution so as to seek the inner positions in the conformation of a peptide in which it is contained when the peptide is in aqueous medium. These residues are also designated "hydrophobic" herein.

Neutra/polar: The residues are not charged at physiological pH, but the residue is attracted by aqueous solution so as to seek the outer positions in the conformation of a peptide in which it is contained when the peptide is in aqueous medium.

It is understood, of course, that in a statistical collection of individual residue molecules some molecules will be charged, and some not, and there will be an attraction for or repulsion from an aqueous medium to a greater or lesser extent. To fit the definition of "charged," a significant percentage (at least approximately 25%) of the individual molecules are charged at physiological pH. The degree of attraction or repulsion required for classification as polar or nonpolar is arbitrary and, therefore, amino acids specifically contemplated by the invention have been classified as one or the other. Most amino acids not specifically named can be classified on the basis of known behavior.

Amino acid residues can be further subclassified as cyclic or noncyclic, and aromatic or nonaromatic, self-explanatory classifications with respect to the side chain substituent groups of the residues, and as small or large. The residue is considered small if it contains a total of 4 carbon atoms or less, inclusive of the carboxyl carbon. Small residues are, of course, always nonaromatic for naturally occurring protein amino acids. .

For the naturally occurring protein amino acids, subclassification according to the foregoing scheme is as follows.

Acidic: Aspartic acid and Glutamic acid;

Basic/noncyclic: Arginine, Lysine;

Basic/cyclic: Histidine;

Neutra/small: Glycine, Serine, Cysteine, Alanine;

Neutral/polar/large/nonaromatic: Threonine, Asparagine, Glutamine;

Neutra/polar/large/aromatic: Tyrosine;

Neutra/nonpolar/large/nonaromatic: Valine, Isoleucine, Leucine, Methionine;

Neutra/nonpolar/large/aromatic: Phenylalanine, and Tryptophan.

The gene-encoded secondary amino acid proline, although technically within the group neutra/nonpolar/large/cyclic and nonaromatic, is a special case due to its known effects on the secondary conformation of peptide chains, and is not, therefore, included in this defined group.

Certain commonly encountered amino acids, which are not encoded by the genetic code, include, for example, beta-alanine (b-Ala), or other omega-amino acids, such as 2,3-diamino propionic (2,3-Dap), 2,4-diaminobutyric (2,4-Dab), 4-amino butyric (g—Abu) and so forth, alpha-aminoisobutyric acid (Aib), sarcosine (Sar), omithine (Om), citrulline (Cit), homoarginine (Har), homolysine (homoLys), n-butylamidinoglycine (Bag), 4-guanidinophenylalanine (4-Gpa), 3-guanidinophenylalanine (3-Gpa), 4-amidinophenylalanine (4-Apa), 3-amidinophenylalanine (3-Apa), 4-aminocyclohexylglycine (4-Acg), 4-aminophenylalanine (4-$NH_2$-Phe), 3-aminophenylalanine (3-$NH_2$-Phe). These also fall conveniently into particular categories.

Based on the above definitions:

Sar, b—Ala, g—Abu, and Aib are neutra/small;

Om, Har, homoLys, Bag, 2,3-Dap, 2,4-Dab, 4-Gpa, 3-Gpa, 4-Apa, 3-Apa, 4-Acg, 4-$NH_2$-Phe, 3-$NH_2$-Phe are basic;

Cit, is neutra/polar/large/nonaromatic; and

The various omega-amino acids are classified according to size as neutra/nonpolar/small (b-Ala, i.e., 3-aminopropionic, 4-aminobutyric) or large (all others).

Amino acid substitutions for those indicated in the structure/formula provided can be included in peptide compounds within the scope of the invention and can be classified within this general scheme according to their structure.

In all of the peptides of the invention, one or more amide linkages (—CO—NH—) may optionally be replaced with another linkage which is an isostere such as —$CH_2NH$—, —$CH_2S$—, —$CH_2CH_2$, —CH=CH— (cis and trans), —$COCH_2$—, —CH(OH)$CH_2$— and —$CH_2SO$—. This replacement can be made by methods known in the art. The following references describe preparation of peptide analogs which include these alternative-linking moieties: Spatola, A. F., *Vega Data* (March 1983), Vol.1, Issue 3, "Peptide Backbone Modifications" (general review); Spatola, A. F., in "Chemistry and Biochemistry of Amino Acids, Peptides and Proteins," B. Weinstein, eds., Marcel Dekker, New York, p. 267 (1983) (general review); Morley, J. S., *Trends Pharm Sci* (1980) pp. 463–468 (general review); Hudson, D., et al.,

*Int J Pept Prot Res* (1979) 14:177–185 (—CH$_2$NH—, —CH$_2$CH$_2$—); Spatola, A. F., et al., *Life Sci* (1986) 38:1243–1249 (—CH$_2$—S); Hann, M. M., *J Chem Soc Perkin Trans I* (1982) 307–314 (—CH=CH—, cis and trans); Almquist, R. G., et al., *J Med Chem* (1980) 23:1392–1398 (—COCH$_2$—); Jennings-White, C., et al., *Tetrahedron Left* (1982) 23:2533 (—COCH$_2$—); Szelke, M., et al., European Application EP 45665; CA:97:39405 (1982) (—CH(OH)CH$_2$—); Holladay, M. W., et al., *Tetrahedron Lett* (1983) 24:4401–4404 (—C(OH)CH$_2$—); and Hruby, V. J., *Life Sci* (1982) 31:189–199 (—CH$_2$—S—).

Preferred Embodiments

In preferred embodiments, the present invention provides compounds of the formula:

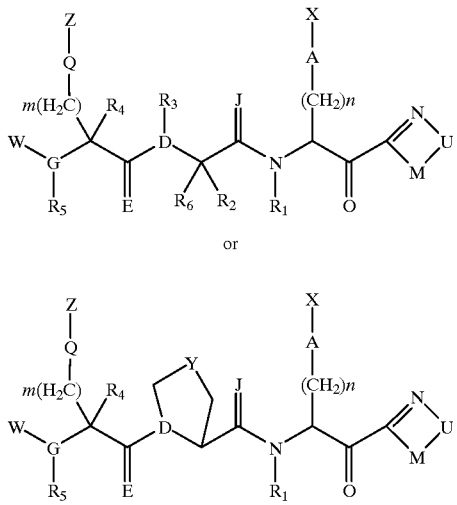

wherein:

m=0,1,2,3,4;

n=0,1,2,3,4;

Y=NH, S, O, CH$_2$, CH—OH, CH$_2$CH$_2$, C=O;

A=piperdinyl, pyrrolidinyl, cyclopropyl, cyclobutyl, cyclopentyl, cyclohexyl, phenyl, C$_{3-6}$heteroaryl, or is absent;

R$_1$=H or C$_{1-3}$alkyl;

J=O or H$_2$;

R$_2$=H or C$_{1-3}$alkyl;

D=N, CH, NCH$_2$, NCH$_2$CH$_2$, CHCH$_2$;

R$_3$=H or C$_{1-3}$alkyl;

E=O or H$_2$;

R$_4$=H or CH$_3$;

M=NH, N—CH$_3$, O, S, SO, SO$_2$ or CH$_2$ or is absent;

Q=piperdinyl, pyrrolidinyl, C$_{3-8}$ cycloalkyl, phenyl, substituted phenyl, naphthyl, pyridyl, or is absent;

G=N, CH, or is H;

R$_5$H or C$_{1-3}$ alkyl or is absent if G is H;

R$_6$=H or CH$_3$;

U=is selected from a group consisting of

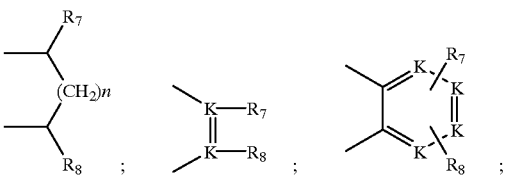

where n=0–4; R$_7$ and R$_8$ are independently selected from a group consisting of H, C$_{1-10}$alkyl, aryl, arylalkyl, halogen, nitro, an amino group of formula —NR$_9$R$_{10}$, an acylamino group of formula —NHCOR$_{11}$, hydroxy, an acyloxy group of formula —OCOR$_{12}$, C$_{1-4}$alkyloxy, C$_{1-4}$alkyl, trifluoromethyl, carboxy, cyano, phenyl, aromatic heterocyclic group as defined herein below, C$_{1-4}$alkyloxycarbonyl, an aminocarbonyl group of formula CONR$_{13}$R$_{14}$, sulfo, sulfonamido of formula SO$_2$NR$_{15}$R$_{16}$ and C$_{1-6}$ hydroxyalkyl; wherein R$_9$, R$_{10}$, R$_{11}$, R$_{12}$, R$_{13}$, R$_{14}$, R$_{15}$, R$_{16}$ are the same or different and =H, C$_{1-6}$ alkyl, C$_{1-3}$arylalkyl or aryl; and if M is absent:

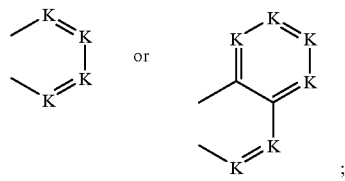

K=C or N;

W=H, arylacyl, heteroarylacyl, arylC$_{1-3}$alkylsulfonyl, arylsulfonyl, substituted arylsulfonyl, arylC$_{1-4}$alkenylsulfonyl, C$_{1-8}$ alkylsulfonyl, heteroarylC$_{1-3}$alkylsulfonyl, heteroarylsulfonyl, aryloxycarbonyl, C$_{1-6}$ alkyloxycarbonyl, arylC$_{1-3}$alkyloxycarbonyl, arylaminocarbonyl, C$_{1-6}$alkylaminocarbonyl, arylC$_{1-3}$alkylaminocarbonyl, HOOC—C$_0$—$_3$alkylcarbonyl, or is absent if G is H;

X=NR'R", NH—C(NR'R")=NH, NH—C(NHR')=NR", NH—C(R')=NR", S— C(NR'R")=NH, S—C(NHR')=NR", C(NR'R")=NH, C(NHR')=NR" or CR'=NR"; where: R',R" are the same or different and =H, C$_{1-6}$alkyl, C$_{1-3}$arylalkyl, aryl or where R'R" forms a cyclic ring containing (CH$_2$)$_p$ where p=2–5;

Z=NR'R", NH—C(NR'R")=NH, NH—C(NHR')=NR", NH—C(R')=NR", S— C(NR'R")=NH, S—C(NHR') =NR", C(NR'R")=NH, C(NHR')=NR" or CR'=NR"; where: R',R" are the same or different and =H, C$_{1-6}$alkyl, C$_{1-3}$arylalkyl, aryl or where R'R" forms a cyclic ring containing (CH$_2$)$_p$ where p=2–5;

and all pharmaceutically acceptable isomers, salts, hydrates, solvates and prodrug derivatives thereof.

Some preferred compounds of the present invention include those of formula:

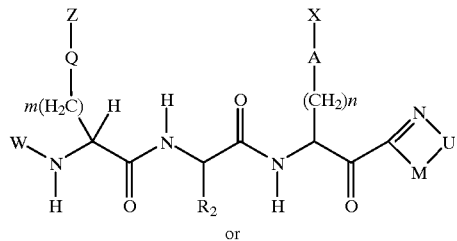

or

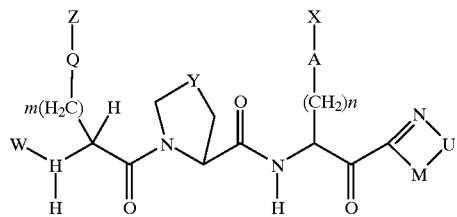

wherein:
m=0,1,2,3,4;
n=0,1,2,3,4;
Y=NH, S, O, CH2, CH—OH, $CH_2CH_2$;
A=piperdinyl, pyrrolidinyl, cyclopropyl, cyclobutyl, cyclopentyl, cyclohexyl, phenyl, $C_{3-6}$heteroaryl, or is absent;
M=NH, N—$CH_3$, O, S, SO, $SO_2$ or

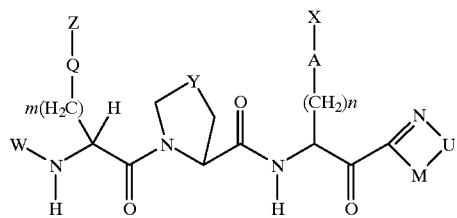

or is absent;
Q=piperdinyl, pyrrolidinyl, $C_{3-8}$ cycloalkyl, phenyl, substituted phenyl, naphthyl, pyridyl, or is absent;
U=is selected from a group consisting of

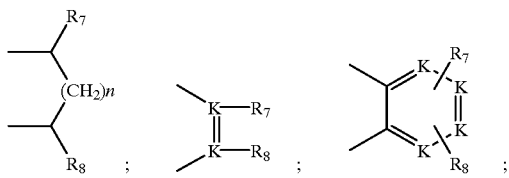

where n=0–4; $R_7$ and $R_8$ are independently selected from a group consisting of H, $C_{1-10}$alkyl, aryl, arylalkyl, halogen, nitro, an amino group of formula —$NR_9R_{10}$, an acylamino group of formula —$NHCOR_{11}$, hydroxy, an acyloxy group of formula —$OCOR_{12}$, $C_{1-4}$alkyloxy, $C_{1-4}$alkyl, trifluoromethyl, carboxy, cyano, phenyl, aromatic heterocyclic group as defined herein below, $C_{1-4}$alkyloxycarbonyl, an aminocarbonyl group of formula $CONR_{13}R_{14}$, sulfo, sulfonamido of formula $SO_2NR_{15}R_{16}$ and $C_{1-6}$hydroxyalkyl; wherein R9, R10, $R_{11}$, $R_{12}$, $R_{13}$, $R_{14}$, $R_{15}$, $R_{16}$ are the same or different and =H, $C_{1-6}$ alkyl, $C_{1-3}$arylalkyl or aryl; and if M is absent:

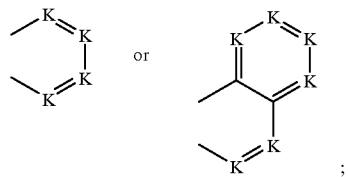

K=C or N;
W=H, arylacyl, heteroarylacyl, aryl$C_{1-3}$alkylsulfonyl, arylsulfonyl, substituted arylsulfonyl, aryl$C_{1-4}$alkenylsulfonyl, $C_{1-8}$ alkylsulfonyl, heteroaryl$C_{1-3}$alkylsulfonyl, heteroarylsulfonyl, aryloxycarbonyl, $C_{1-6}$ alkyloxycarbonyl, aryl$C_{1-3}$alkyloxycarbonyl, arylaminocarbonyl, $C_{1-6}$alkylaminocarbonyl, aryl$C_{1-3}$alkylaminocarbonyl, HOOC—$C_0$—$_3$alkylcarbonyl, or is absent if G is H;
X=NR'R", NH—C(NR'R")=NH, NH—C(NHR')=NR", NH—C(R')=NR", S—C(NR'R")=NH, S—C(NHR')=NR", C(NR'R")=NH, C(NHR')=NR" or CR'=NR"; where: R',R" are the same or different and =H, $C_{1-6}$alkyl, $C_{1-3}$arylalkyl, aryl or where R'R" forms a cyclic ring containing $(CH_2)_p$ where p=2–5;
Z=NR'R", NH—C(NR'R")=NH, NH—C(NHR')=NR", NH—C(R')=NR", S—C(NR'R")=NH, S—C(NHR')=NR", C(NR'R")=NH, C(NHR')=NR" or CR'=NR"; where: R',R" are the same or different and =H, $C_{1-6}$alkyl, $C_{1-3}$arylalkyl, aryl or where R'R" forms a cyclic ring containing $(CH_2)_p$ where p=2–5;
and all pharmaceutically acceptable isomers, salts, hydrates, solvates and prodrug derivatives thereof.

A preferred substituent Y is S, O, $CH_2$, $CH_2CH_2$.
A preferred substituent A is piperdinyl, pyrrolidinyl, cyclopentyl, cyclohexyl, phenyl, $C_{3-6}$heteroaryl, or is absent.
A preferred substituent D is N, CH, $NCH_2$.
A preferred substituent M is NH, O, S, $CH_2$ or is absent.
A preferred substituent Q is piperdinyl, pyrrolidinyl, $C_{3-8}$ cycloalkyl, phenyl, substituted phenyl, or is absent.
A preferred substituent U is selected from

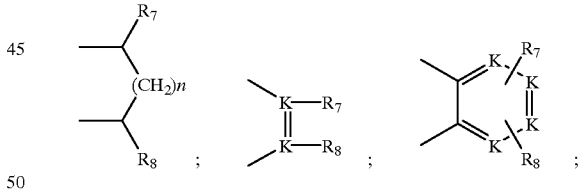

where n=0–2; $R_7$ and $R_8$ are independently selected from a group consisting of H, $C_{1-10}$alkyl, aryl, arylalkyl, halogen, nitro, trifluoromethyl, carboxy, or cyano; and if M is absent:

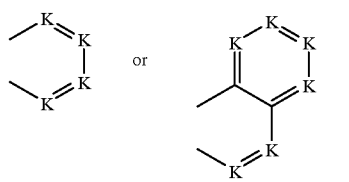

A preferred substituent K is C or N.
A preferred substituent W is aryl$C_{1-3}$alkylsulfonyl, arylsulfonyl, substituted arylsulfonyl, aryl$C_{1-4}$alkenylsulfonyl, $C_{1-8}$ alkylsulfonyl, heteroaryl$C_{1-3}$ alkylsulfonyl, heteroarylsulfonyl, $C_{1-6}$ alkyloxycarbonyl, aryl$C_{1-3}$alkyloxycarbonyl.

A preferred substituent X is NR'R", NH—C(NR'R")=NH, NH—C(NHR')=NR",NH—C(R')=NR", S—C(NR'R")=NH, S—C(NHR')=NR", C(NR'R")=NH, C(NHR')=NR"; where: R',R" are the same or different and =H, $C_{1-6}$alkyl.

A preferred substituent Z is , NH—C(NR'R")=NH, NH—C(NHR')=NR',NH—C(R')=NR", S—C(NR'R")=NH, S—C(NHR')=NR", C(NR'R")=NH, C(NHR')=NR"; where: R',R" are the same or different and =H, $C_{1-6}$alkyl.

Preferred compounds as a whole may be selected from any combination of the formulas presented in this specification with one or more of the preferred groupings of substituents at a particular location.

Some preferred embodiments of the invention are shown in the following Table 1.

TABLE 1

| STRUCTURE | Inhibitory Activity ($IC_{50}$) μM | | |
|---|---|---|---|
| | Factor Xa | Pro-thrombinase | Thrombin |
| H-D-Arg-Gly-Arg-thiazole | 0.011 | 0.010 | 41 |
| BnSO$_2$-(D)-Arg-Gly-Arg-thiazole | 0.00065 | 0.00045 | 10 |

Other preferred compounds of the present invention are shown but not limited to the following list of compounds which have the general structure:

W—(Basic amino acid)—(Neutra/small amino acid)—(Arg or Basic amino acid)—Heterocycle PhCH$_2$CH$_2$—SO$_2$—(D)—Arg—Gly—Arg—Thiazole
C$_6$H$_{11}$CH$_2$CH$_2$SO$_2$—(D)—Arg—Gly—Arg—Thiazole
Me$_3$C—C$_6$H$_4$SO$_2$—(D)—Arg—Gly—Arg—Thiazole
C$_{10}$H$_7$SO$_2$—(D)—Arg—Gly—Arg—Thiazole
Me$_3$SiCH$_2$CH$_2$CH$_2$SO$_2$—(D)—Arg—Gly—Arg—Thiazole
BnSO$_2$—(D)—4—Apa—Gly—Arg—Thiazole
BnSO$_2$—(D)—4—Gpa—Gly—Arg—Thiazole
BnSO$_2$—(D)—Acg—Gly—Arg—Thiazole
BnSO$_2$—(D)—homo—Lys—Gly—Arg—Thiazole
BnSO$_2$—(D)—Arg—Sar—Arg—Thiazole
BnSO$_2$—(D)—Arg—Pro—Arg—Thiazole
BnSO$_2$—(D)—Arg—Gly—4—Acg—Thiazole
BnSO$_2$—(D)—Arg—Gly—(3—NH2—Phe)—Thiazole
BnSO$_2$—(D)—Arg—Gly—(4—NH2—Phe)—Thiazole
BnSO$_2$—(D)—Arg—Gly—Gpa—Thiazole
Boc—D—(2,3-Dap)—Gly—Arg—Thiazole
Boc—D—(2,4-Dab)—Gly—Arg—Thiazole
g—Abu—Gly—Arg—Thiazole
Boc—D—Orn—Gly—Arg—Thiazole
Boc—D—homoLys—Gly—Arg—Thiazole
Boc—Bag—Gly—Arg—Thiazole
Boc—D—4-Gpa—Gly—Arg—Thiazole
Boc—D—3-Gpa—Gly—Arg—Thiazole
Boc—D—4-Apa—Gly—Arg—Thiazole
Boc—D—3-Apa—Gly—Arg—Thiazole
Boc—D—4-Acg—Gly—Arg—Thiazole
Boc—D—(4-NH$_2$Phe)—Gly—Arg—Thiazole
Boc—D—(3-NH$_2$Phe)—Gly—Arg—Thiazole
BnSO$_2$—D—(2,3-Dap)—Gly—Arg—Thiazole
BnSO$_2$—D—(2,4-Dab)—Gly—Arg—Thiazole
BnSO$_2$—D—Orn—Gly—Arg—Thiazole
BnSO$_2$-Bag—Gly—Arg—Thiazole
BnSO$_2$—D—3-Gpa—Gly—Arg—Thiazole
BnSO$_2$—D—3-Apa-Gly-Arg—Thiazole
BnSO$_2$—D—(4-NH$_2$Phe)—Gly—Arg—Thiazole
BnSO$_2$—D—(3-NH$_2$Phe)—Gly—Arg—Thiazole
BnSO$_2$—D—(2,3-Dap)—Gly—Arg—Benzothiazole
BnSO$_2$—D—(2,4-Dab)—Gly—Arg—Benzothiazole
BnSO$_2$—D—Orn—Gly—Arg—Benzothiazole
BnSO$_2$—Bag—Gly—Arg—Benzothiazole
BnSO$_2$—D—4-Gpa—Gly—Arg—Benzothiazole
BnSO$_2$—D—3-Gpa—Gly—Arg—Benzothiazole
BnSO$_2$—D—4-Apa—Gly—Arg—Benzothiazole
BnSO$_2$—D—3-Apa—Gly—Arg—Benzothiazole
BnSO$_2$—D—4-Acg—Gly—Arg—Benzothiazole
BnSO$_2$—D—(4-NH$_2$Phe)—Gly—Arg—Benzothiazole
BnSO$_2$—D—(3-NH$_2$Phe)—Gly—Arg—Benzothiazole
BnSO$_2$—D—Arg—Gly—(2,4-Dab)-Benzothiazole
BnSO$_2$—D—Arg—Gly—(homoLys)-Benzothiazole
BnSO$_2$—D—Arg—Gly—(4-Gpa)-Benzothiazole
BnSO$_2$—D—Arg—Gly—(3-Gpa)-Benzothiazole
BnSO$_2$—D—Arg—Gly—(4-Apa)-Benzothiazole
BnSO$_2$—D—Arg—Gly—(3-Apa)-Benzothiazole
BnSO$_2$—D—Arg—Gly—(4-NH$_2$Phe)-Benzothiazole
BnSO$_2$—D—Arg—Gly—(3-NH$_2$Phe)-Benzothiazole
Me$_3$SiCH$_2$CH$_2$CH$_2$SO$_2$—(D)—Arg—Gly—Arg—Benzothiazole
BnSO$_2$—(D)—homo—Lys—Gly—Arg—Benzothiazole
BnSO$_2$—(D)—homo—Lys—Gly—Arg—Benzoxazole
PhCH$_2$CH$_2$—SO$_2$—(D)—Arg—Gly—Arg—Benzothiazole
BnSO$_2$—(D)—Arg—Sar—Arg—Benzothiazole
BnSO$_2$—(D)—Arg—Pro—Arg—Benzothiazole
BnSO$_2$—(D)—Arg—Gly—Acg—Benzothiazole
BnSO$_2$—(D)—Arg—Gly—Arg—Benzothiazole
PhCH$_2$CH$_2$SO$_2$—(D)—Arg—Gly—4-Acg—Benzothiazole
BnSO$_2$—(D)—Arg—Gly—Arg—Oxazole
Boc—D—(2,3-Dap)—Gly—Arg—Oxazole
Boc—D—(2,4-Dab)—Gly—Arg—Oxazole
g—Abu—Gly—Arg—Oxazole
Boc—D—Orn—Gly—Arg—Oxazole
Boc—D—homoLys—Gly—Arg—Oxazole
Boc—Bag—Gly—Arg—Oxazole
Boc—D—4-Gpa—Gly—Arg—Oxazole
Boc—D—3-Gpa—Gly—Arg—Oxazole
Boc—D—4-Apa—Gly—Arg—Oxazole
Boc—D—3-Apa—Gly—Arg—Oxazole
Boc—D—4-Acg—Gly—Arg—Oxazole
Boc—D—(4-NH$_2$Phe)—Gly—Arg—Oxazole
Boc—D—(3-NH$_2$Phe)—Gly—Arg—Oxazole
BnSO$_2$—D—(2,3-Dap)—Gly—Arg—Oxazole
BnSO$_2$—D—(2,4-Dab)—Gly—Arg—Oxazole
BnSO$_2$—D—Orn—Gly—Arg—Oxazole
BnSO$_2$—Bag—Gly—Arg—Oxazole
BnSO$_2$—D—3-Gpa—Gly—Arg—Oxazole BnSO₂—D—3-Apa—Gly—Arg—Oxazole
BnSO₂—D—(4-NH₂Phe)—Gly—Arg—Oxazole
BnSO₂—D—(3-NH₂Phe)—Gly—Arg—Oxazole
BnSO₂—D—(2,3-Dap)—Gly—Arg—Oxazole
BnSO₂—D—(2,4-Dab)—Gly—Arg—Oxazole
BnSO₂—D—Orn—Gly—Arg—Oxazole
BnSO₂—Bag—Gly—Arg—Oxazole
BnSO₂—D—4-Gpa—Gly—Arg—Oxazole
BnSO₂—D—3-Gpa—Gly—Arg—Oxazole
BnSO₂—D—4-Apa—Gly—Arg—Oxazole
BnSO₂—D—3-Apa—Gly—Arg—Oxazole
BnSO₂—D—4-Acg—Gly—Arg—Oxazole
BnSO₂—D—(4-NH₂Phe)—Gly—Arg—Oxazole
BnSO₂—D—(3-NH₂Phe)—Gly—Arg—Oxazole
BnSO₂—D—Arg—Gly—(2,4-Dab)—Oxazole
BnSO₂—D—Arg—Gly—(homoLys)—Oxazole
BnSO₂—D—Arg—Gly—(4-Gpa)—Oxazole
BnSO₂—D—Arg—Gly—(3-Gpa)—Oxazole
BnSO₂—D—Arg—Gly—(4-Apa)—Oxazole
BnSO₂—D—Arg—Gly—(3-Apa)—Oxazole
BnSO₂—D—Arg—Gly—(4-NH₂Phe)—Oxazole
BnSO₂—D—Arg—Gly—(3-NH₂Phe)—Oxazole
BnSO₂—D—(2,3-Dap)—Gly—Arg—Benzoxazole
BnSO₂—D—(2,4-Dab)—Gly—Arg—Benzoxazole
BnSO₂—D—Orn—Gly—Arg—Benzoxazole
BnSO₂—Bag—Gly—Arg—Benzoxazole
BnSO₂—D—4-Gpa—Gly—Arg—Benzoxazole
BnSO₂—D—3-Gpa—Gly—Arg—Benzoxazole
BnSO₂—D—4-Apa—Gly—Arg—Benzoxazole
BnSO₂—D—3-Apa—Gly—Arg—Benzoxazole
BnSO₂—D—4-Acg—Gly—Arg—Benzoxazole
BnSO₂—D—(4-NH₂Phe)—Gly—Arg—Benzoxazole
BnSO₂—D—(3-NH₂Phe)—Gly—Arg—Benzoxazole
BnSO₂—D—Arg—Gly—(2,4-Dab)—Benzoxazole
BnSO₂—D—Arg—Gly—(homoLys)—Benzoxazole
BnSO₂—D—Arg—Gly—(4-Gpa)—Benzoxazole
BnSO₂—D—Arg—Gly—(3-Gpa)—Benzoxazole
BnSO₂—D—Arg—Gly—(4-Apa)—Benzoxazole
BnSO₂—D—Arg—Gly—(3-Apa)—Benzoxazole
BnSO₂—D—Arg—Gly—(4-NH₂Phe)—Benzoxazole
BnSO₂—D—Arg—Gly—(3-NH₂Phe)—Benzoxazole
Me₃SiCH₂CH₂CH₂SO₂—(D)—Arg—Gly—Arg—Benzoxazole
BnSO₂—(D)—homo—Lys—Gly—Arg—Benzoxazole
BnSO₂—(D)—homo—Lys—Gly—Arg—Benzoxazole
PhCH₂CH₂—SO₂—(D)—Arg—Gly—Arg—Benzoxazole
BnSO₂—(D)—Arg—Sar—Arg—Benzoxazole
BnSO₂—(D)—Arg—Pro—Arg—Benzoxazole
BnSO₂—(D)—Arg—Gly—Acg—Benzoxazole
BnSO₂—(D)—Arg—Gly—Arg—Benzoxazole
PhCH₂CH₂SO₂—(D)—Arg—Gly—4-Acg—Benzoxazole
BnSO₂—(D)—Arg—Gly—Arg—Benzoxazole
BnSO₂—(D)—Arg—Gly—Acg—Benzoxazole
PhCH₂CH₂—SO₂—(D)—Arg—Gly—Arg—Benzoxazole
PhCH₂CH₂—SO₂—(D)—Arg—Gly—4-Acg—Benzoxazole
Me₃SiCH₂CH₂CH₂SO₂—(D)—Arg—Gly—Arg—Benzoxazole
BnSO₂—(D)—Arg—Gly—Arg—Oxazoline
Boc—D—(2,3-Dap)—Gly—Arg—Oxazoline
Boc—D—(2,4-Dab)—Gly—Arg—Oxazoline
g—Abu—Gly—Arg—Oxazoline
Boc—D—Orn—Gly—Arg—Oxazoline
Boc—D—homoLys—Gly—Arg—Oxazoline
Boc—Bag—Gly—Arg—Oxazoline
Boc—D—4-Gpa—Gly—Arg—Oxazoline
Boc—D—3-Gpa—Gly—Arg—Oxazoline
Boc—D—4-Apa—Gly—Arg—Oxazoline
Boc—D—3-Apa—Gly—Arg—Oxazoline
Boc—D—4-Acg—Gly—Arg—Oxazoline
Boc—D—(4-NH₂Phe)—Gly—Arg—Oxazoline
Boc—D—(3-NH₂Phe)—Gly—Arg—Oxazoline
BnSO₂—D—(2,3-Dap)—Gly—Arg—Oxazoline
BnSO₂—D—(2,4-Dab)—Gly—Arg—Oxazoline
BnSO₂—D—Orn—Gly—Arg—Oxazoline
BnSO₂—Bag—Gly—Arg—Oxazoline
BnSO₂—D—3-Gpa—Gly—Arg—Oxazoline
BnSO₂—D—3-Apa—Gly—Arg—Oxazoline
BnSO₂—D—(4-NH₂Phe)—Gly—Arg—Oxazoline
BnSO₂—D—(3-NH₂Phe)—Gly—Arg—Oxazoline
BnSO₂—D—(2,3-Dap)—Gly—Arg—Oxazoline
BnSO₂—D—(2,4-Dab)—Gly—Arg—Oxazoline
BnSO₂—D—Orn—Gly—Arg—Oxazoline
BnSO₂—Bag—Gly—Arg—Oxazoline
BnSO₂—D—4-Gpa—Gly—Arg—Oxazoline
BnSO₂—D—3-Gpa—Gly—Arg—Oxazoline
BnSO₂—D—4-Apa—Gly—Arg—Oxazoline
BnSO₂—D—3-Apa—Gly—Arg—Oxazoline
BnSO₂—D—4-Acg—Gly—Arg—Oxazoline
BnSO₂—D—(4-NH₂Phe)—Gly—Arg—Oxazoline
BnSO₂—D—(3-NH₂Phe)—Gly—Arg—Oxazoline
BnSO₂—D—Arg—Gly—(2,4-Dab)—Oxazoline
BnSO₂—D—Arg—Gly—(homoLys)-Oxazoline
BnSO₂—D—Arg—Gly—(4-Gpa)—Oxazoline
BnSO₂—D—Arg—Gly—(3-Gpa)—Oxazoline
BnSO₂—D—Arg—Gly—(4-Apa)—Oxazoline
BnSO₂—D—Arg—Gly—(3-Apa)—Oxazoline
BnSO₂—D—Arg—Gly—(4-NH₂Phe)—Oxazoline
BnSO₂—D—Arg—Gly—(3-NH₂Phe)—Oxazoline
BnSO₂—(D)—Arg—Gly—Arg—Imidazole
BnSO₂—(D)—Arg—Gly—Arg—Pyridine
BnSO₂—(D)—Arg—Gly—Arg—2-(1-methyl-tetrazole)
BnSO₂—(D)—Arg—Gly—Arg—2-(4-methyl-tetrazole)

This invention also encompasses prodrug derivatives of the compounds contained herein. The term "prodrug" to a pharmacologically inactive derivative of a parent drug molecule that requires biotransformation, either spontaneous or enzymatic, within the organism to release the active drug. Prodrugs are variations or derivatives of the compounds of this invention which have metabolically cleavable groups and become, by solvolysis under physiological conditions, or by enzymatic degradation the compounds of the invention which are pharmaceutically active in vivo. Prodrug compounds of this invention may be called single, double, triple etc., depending on the number of biotransformation steps required to release the active drug within the organism, and indicating the number of functionalities present in a precursor-type form. Prodrug forms often offer advantages of solubility, tissue compatibility, or delayed release in the mammalian organism (see, Bundgard, H., *Design of Prodrugs*, pp. 7–9, 21–24, Elsevier, Amsterdam 1985 and Silverman, R. B., *The Organic Chemistry of Drug Design and Drug Action*, pp. 352–401, Academic Press, San Diego, Calif., 1992). Prodrugs commonly known in the art include acid derivatives well known to practitioners of the art, such as, for example, esters prepared by reaction of the parent acids with a suitable alcohol, or amides prepared by reaction of the parent acid compound with an amine, or basic groups reacted to form an acylated base derivative. Moreover, the prodrug derivatives of this invention may be combined with other features herein taught to enhance bioavailability.

Preparation of Compounds

The compounds of the present invention may be synthesized by either solid or liquid phase methods described and referenced in standard textbooks, or by a combination of both methods. These methods are well known in the art. See, Bodanszky, M., in "The Principles of Peptide Synthesis", Hafner, K., Rees, C. W., Trost, B. M., Lehn, J. -M., Schleyer, P. v -R., Zahradnik, R., Eds., Springer-Verlag, Berlin, 1984. Starting materials are commercially available reagents and reactions are carried out in standard laboratory glassware and reaction vessels under reaction conditions of standard temperature and pressure, except where otherwise indicated.

The ketoheterocyclic compounds of the invention can be prepared by methods described by Dondoni, A. et. at., Synthesis, 1162–1176 (1993); Edwards, P. D., et. al., J. Amer. Chem. Soc., 114, 1854–1863 (1992); Tsutsumi, S., et. al., J. Med. Chem. 37, 3492–3502 (1994); and Edwards, P. D., et. al., J. Med. Chem. 38, 76–85 (1995).

The starting materials used in any of these methods are commercially available from chemical vendors such as Aldrich, Sigma, Nova Biochemicals, Bachem Biosciences, and the like, or may be readily synthesized by known procedures.

During the synthesis of these compounds, the functional groups of the amino acid derivatives used in these methods are protected by blocking groups to prevent cross reaction during the coupling procedure. Examples of suitable blocking groups and their use are described in "The Peptides: Analysis, Synthesis, Biology", Academic Press, Vol. 3 (Gross, E. & Meienhofer, J., Eds., 1981) and Vol.9 (, S. &., Eds., 1987), the disclosures of which are incorporated herein by reference.

Two exemplary synthesis schemes are outlined directly below, and the specific syntheses are described in the Examples. The reaction products are isolated and purified by conventional methods, typically by solvent extraction into a compatible solvent. The products may be further purified by column chromatography or other appropriate methods.

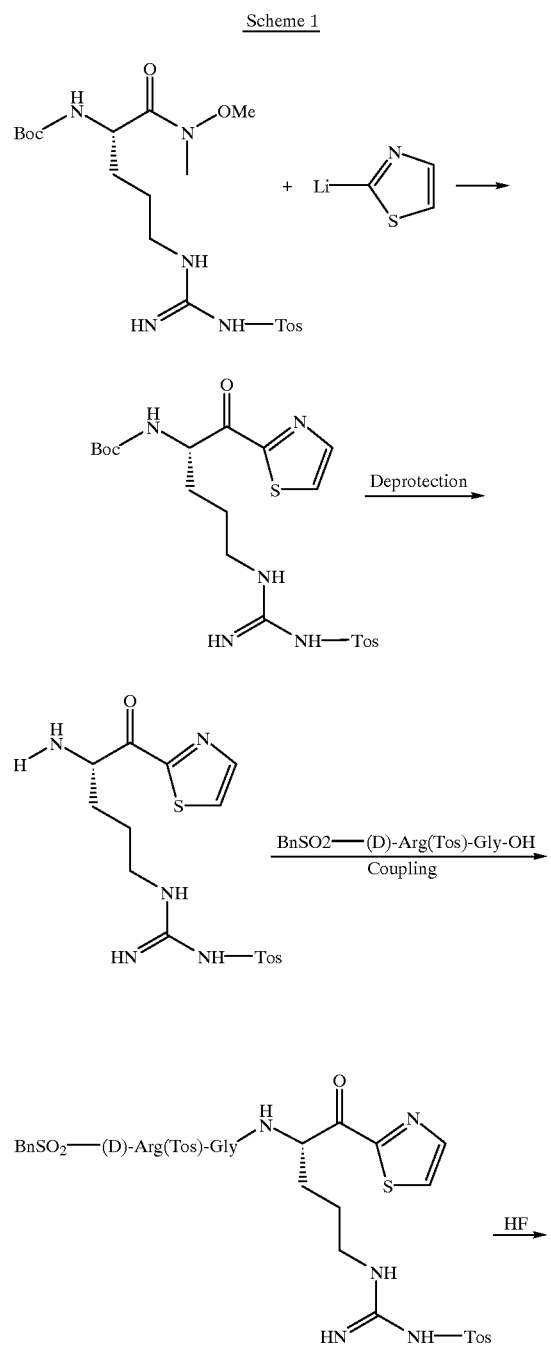

Scheme 1

-continued

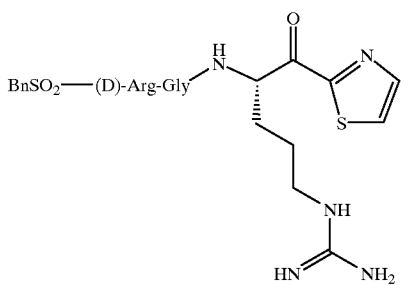

and organic acids and bases. Such salts are within the scope of this invention. Non-toxic and physiologically compatible salts are particularly useful although other less desirable salts may have use in the processes of isolation and purification.

A number of methods are useful for the preparation of the salts described above and are known to those skilled in the art. For example, reaction of the free acid or free base form of a compound of the structures recited above with one or more molar equivalents of the desired acid or base in a solvent or solvent mixture in which the salt is insoluble, or in a solvent like water after which the solvent is removed by evaporation, distillation or freeze drying. Alternatively, the free acid or base form of the product may be passed over an ion exchange resin to form the desired salt or one salt form of the product may be converted to another using the same general process.

Diagnostic applications of the compounds of this invention will typically utilize formulations such as solution or Scheme 2

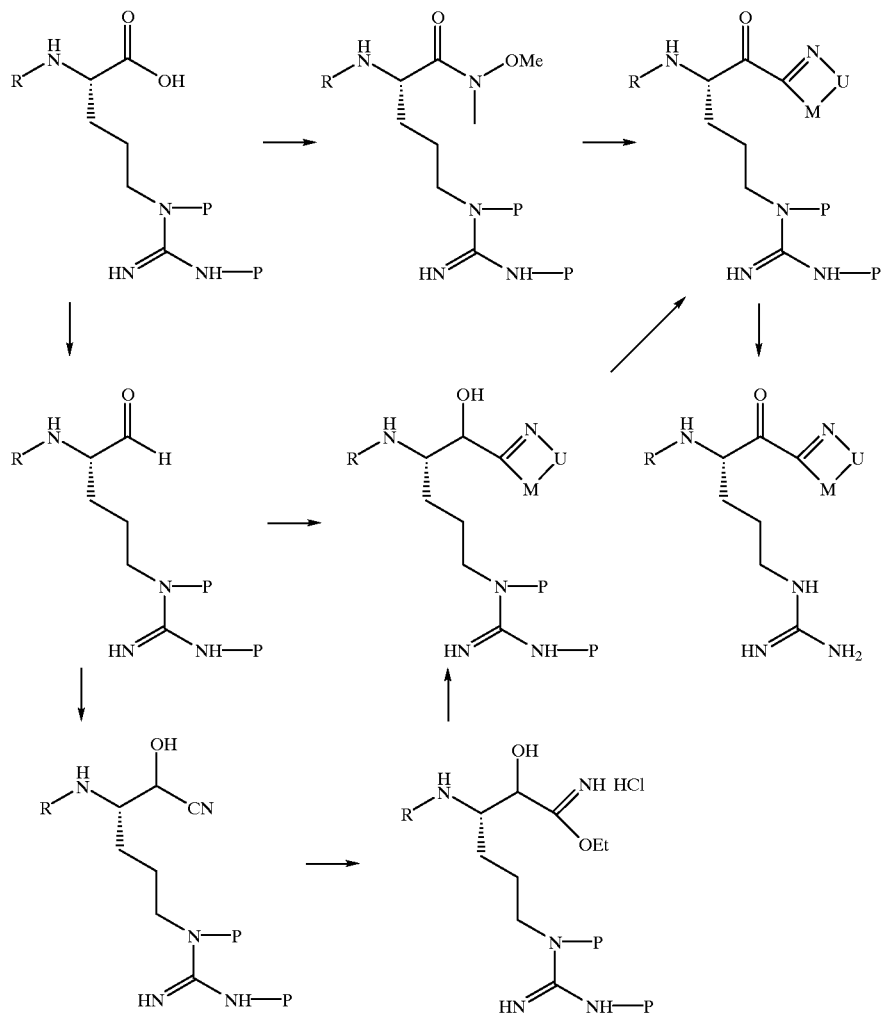

P=Protecting group; R=Protecting group, protected or substituted amino acid, or protected or substituted dipeptide unit Compositions and Formulations The compounds of this invention may be isolated as the free acid or base or converted to salts of various inorganic suspension. In the management of thrombotic disorders the compounds of this invention may be utilized in compositions such as tablets, capsules or elixirs for oral administration, suppositories, sterile solutions or suspensions or injectable administration, and the like, or incorporated into shaped articles. Subjects in need of treatment (typically mammalian) using the compounds of this invention can be administered dosages that will provide optimal efficacy. The dose and method of administration will vary from subject to subject and be dependent upon such factors as the type of mammal being treated, its sex, weight, diet, concurrent medication, overall clinical condition, the particular compounds employed, the specific use for which these compounds are employed, and other factors which those skilled in the medical arts will recognize.

Formulations of the compounds of this invention are prepared for storage or administration by mixing the compound having a desired degree of purity with physiologically acceptable carriers, excipients, stabilizers etc., and may be provided in sustained release or timed release formulations. Acceptable carriers or diluents for therapeutic use are well known in the pharmaceutical field, and are described, for example, in *Remington's Pharmaceutical Sciences*, Mack Publishing Co., (A. R. Gennaro edit. 1985). Such materials are nontoxic to the recipients at the dosages and concentrations employed, and include buffers such as phosphate, citrate, acetate and other organic acid salts, antioxidants such as ascorbic acid, low molecular weight (less than about ten residues) peptides such as polyarginine, proteins, such as serum albumin, gelatin, or immunoglobulins, hydrophilic polymers such as polyvinalpyrrolidinone, amino acids such as glycine, glutamic acid, aspartic acid, or arginine, monosaccharides, disaccharides, and other carbohydrates including cellulose or its derivatives, glucose, mannose or dextrins, chelating agents such as EDTA, sugar alcohols such as mannitol or sorbitol, counterons such as sodium and/or nonionic surfactants such as Tween, Pluronics or polyethyleneglycol.

Dosage formulations of the compounds of this invention to be used for therapeutic administration must be sterile. Sterility is readily accomplished by filtration through sterile membranes such as 0.2 micron membranes, or by other conventional methods. Formulations typically will be stored in lyophilized form or as an aqueous solution. The pH of the preparations of this invention typically will be between 3 and 11, more preferably from 5 to 9 and most preferably from 7 to 8. It will be understood that use of certain of the foregoing excipients, carriers, or stabilizers will result in the formation of cyclic polypeptide salts. While the preferred route of administration is by injection, other methods of administration are also anticipated such as intravenously (bolus and/or infusion), subcutaneously, intramuscularly, colonically, rectally, nasally or intraperitoneally, employing a variety of dosage forms such as suppositories, implanted pellets or small cylinders, aerosols, oral dosage formulations and topical formulations such as ointments, drops and dermal patches. The compounds of this invention are desirably incorporated into shaped articles such as implants which may employ inert materials such as biodegradable polymers or synthetic silicones, for example, Silastic, silicone rubber or other polymers commercially available.

The compounds of this invention may also be administered in the form of liposome delivery systems, such as small unilamellar vesicles, large unilamellar vesicles and multilamellar vesicles. Liposomes can be formed from a variety of lipids, such as cholesterol, stearylamine or phosphatidylcholines.

The compounds of this invention may also be delivered by the use of antibodies, antibody fragments, growth factors, hormones, or other targeting moieties, to which the compound molecules are coupled. The compounds of this invention may also be coupled with suitable polymers as targetable drug carriers. Such polymers can include polyvinylpyrrolidone, pyran copolymer, polyhydroxypropyl-methacrylamide-phenol, polyhydroxyethyl-aspartamide-phenol, or polyethyleneoxide-polylysine substituted with palmitoyl residues. Furthermore, the factor Xa inhibitors of this invention may be coupled to a class of biodegradable polymers useful in achieving controlled release of a drug, for example polylactic acid, polyglycolic acid, copolymers of polylactic and polyglycolic acid, poly-epsilon caprolactone, polyhydroxy butyric acid, polyorthoesters, polyacetals, polydihydropyrans, polycyanoacrylates and cross linked or amphipathic block copolymers of hydrogels. Polymers and semipermeable polymer matrices may be formed into shaped articles, such as valves, stents, tubing, prostheses and the like.

Therapeutic compound liquid formulations generally are placed into a container having a sterile access port, for example, an intravenous solution bag or vial having a stopper pierceable by hypodermic injection needle.

Therapeutically effective dosages may be determined by either in vitro or in vivo methods. For each particular compound of the present invention, individual determinations may be made to determine the optimal dosage required. The range of therapeutically effective dosages will naturally be influenced by the route of administration, the therapeutic objectives, and the condition of the patient. For injection by hypodermic needle, it may be assumed the dosage is delivered into the body's fluids. For other routes of administration, the absorption efficiency must be individually determined for each inhibitor by methods well known in pharmacology. Accordingly, it may be necessary for the therapist to titer the dosage and modify the route of administration as required to obtain the optimal therapeutic effect. The determination of effective dosage levels, that is, the dosage levels necessary to achieve the desired result, will be within the ambit of one skilled in the art. Typically, applications of compound are commenced at lower dosage levels, with dosage levels being increased until the desired effect is achieved.

A typical dosage might range from about 0.001 mg/kg to about 1000 mg/kg, preferably from about 0.01 mg/kg to about 100 mg/kg, and more preferably from about 0.10 mg/kg to about 20 mg/kg. Advantageously, the compounds of this invention may be administered several times daily, and other dosage regimens may also be useful.

Typically, about 0.5 to 500 mg of a compound or mixture of compounds of this invention, as the free acid or base form or as a pharmaceutically acceptable salt, is compounded with a physiologically acceptable vehicle, carrier, excipient, binder, preservative, stabilizer, dye, flavor etc., as called for by accepted pharmaceutical practice. The amount of active ingredient in these compositions is such that a suitable dosage in the range indicated is obtained.

Typical adjuvants which may be incorporated into tablets, capsules and the like are a binder such as acacia, corn starch or gelatin, and excipient such as microcrystalline cellulose, a disintegrating agent like corn starch or alginic acid, a lubricant such as magnesium stearate, a sweetening agent such as sucrose or lactose, or a flavoring agent. When a dosage form is a capsule, in addition to the above materials it may also contain a liquid carrier such as water, saline, a fatty oil. Other materials of various types may be used as coatings or as modifiers of the physical form of the dosage unit. Sterile compositions for injection can be formulated according to conventional pharmaceutical practice. For example, dissolution or suspension of the active compound in a vehicle such as an oil or a synthetic fatty vehicle like ethyl oleate, or into a liposome may be desired. Buffers, preservatives, antioxidants and the like can be incorporated according to accepted pharmaceutical practice.

In practicing the methods of this invention, the compounds of this invention may be used alone or in combination, or in combination with other therapeutic or diagnostic agents. In certain preferred embodiments, the compounds of this inventions may be coadministered along with other compounds typically prescribed for these conditions according to generally accepted medical practice, such as anticoagulant agents, thrombolytic agents, or other antithrombotics, including platelet aggregation inhibitors, tissue plasminogen activators, urokinase, prourokinase, streptokinase, heparin, aspirin, or warfarin. The compounds of this invention can be utilized in vivo, ordinarily in mammals such as primates, such as humans, sheep, horses, cattle, pigs, dogs, cats, rats and mice, or in vitro.

The preferred compounds of the present invention are characterized by their ability to inhibit thrombus formation with acceptable effects on classical measures of coagulation parameters, platelets and platelet function, and acceptable levels of bleeding complications associated with their use. Conditions characterized by undesired thrombosis would include those involving the arterial and venous vasculature.

With respect to the coronary arterial vasculature, abnormal thrombus formation characterizes the rupture of an established atherosclerotic plaque which is the major cause of acute myocardial infarction and unstable angina, as well as also characterizing the occlusive coronary thrombus formation resulting from either thrombolytic therapy or percutaneous transluminal coronary angioplasty (PTCA).

With respect to the venous vasculature, abnormal thrombus formation characterizes the condition observed in patients undergoing major surgery in the lower extremities or the abdominal area who often suffer from thrombus formation in the venous vasculature resulting in reduced blood flow to the affected extremity and a predisposition to pulmonary embolism. Abnormal thrombus formation further characterizes disseminated intravascular coagulopathy commonly occurs within both vascular systems during septic shock, certain viral infections and cancer, a condition wherein there is rapid consumption of coagulation factors and systemic coagulation which results in the formation of life-threatening thrombi occurring throughout the microvasculature leading to widespread organ failure.

The compounds of this present invention, selected and used as disclosed herein, are believed to be useful for preventing or treating a condition characterized by undesired thrombosis, such as (a) the treatment or prevention of any thrombotically mediated acute coronary syndrome including myocardial infarction, unstable angina, refractory angina, occlusive coronary thrombus occurring post-thrombolytic therapy or post-coronary angioplasty, (b) the treatment or prevention of any thrombotically mediated cerebrovascular syndrome including embolic stroke, thrombotic stroke or transient ischemic attacks, (c) the treatment or prevention of any thrombotic syndrome occurring in the venous system including deep venous thrombosis or pulmonary embolus occurring either spontaneously or in the setting of malignancy, surgery or trauma, (d) the treatment or prevention of any coagulopathy including disseminated intravascular coagulation (including the setting of septic shock or other infection, surgery, pregnancy, trauma or malignancy and whether associated with multi-organ failure or not), thrombotic thrombocytopenic purpura, thromboangiitis obliterans, or thrombotic disease associated with heparin induced thrombocytopenia, (e) the treatment or prevention of thrombotic complications associated with extracorporeal circulation (e.g. renal dialysis, cardiopulmonary bypass or other oxygenation procedure, plasmapheresis), (f) the treatment or prevention of thrombotic complications associated with instrumentation (e.g. cardiac or other intravascular catheterization, intra-aortic balloon pump, coronary stent or cardiac valve), and (g) those involved with the fitting of prosthetic devices.

Anticoagulant therapy is also useful to prevent coagulation of stored whole blood and to prevent coagulation in other biological samples for testing or storage. Thus the compounds of this invention can be added to or contacted with any medium containing or suspected to contain factor Xa and in which it is desired that blood coagulation be inhibited, e.g., when contacting the mammal's blood with material such as vascular grafts, stents, orthopedic prostheses, cardiac stents, valves and prostheses, extra corporeal circulation systems and the like.

Without further description, it is believed that one of ordinary skill in the art can, using the preceding description and the following illustrative examples, make and utilize the compounds of the present invention and practice the claimed methods. The following working examples therefore, specifically point out preferred embodiments of the present invention, and are not to be construed as limiting in any way the remainder of the disclosure.

EXAMPLE 1

Preparation of Boc—Arg(Tos)—N(Me)OMe

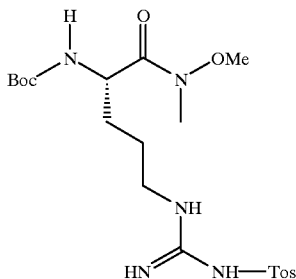

To a suspension of Boc—Arg(Tos)—OH (2 g, 4.7 mmol) in DMF (20 mL) at 0° C. was added MeNHOMe.HCl (1 g, 10.3 mmol), DIEA (2 mL) and BOP (2.5 g, 5.6 mmol). The solution was stirred at 0° C. for 10 h. DMF was evaporated in vacuo. The oily residue was dissolved in EtOAc (200 mL) and water (20 mL). The organic layer was washed with sat. NaHCO$_3$, water (20 mL), 1 M HCl (10 mL) and sat. NaCl (2×20 mL). The organic layer was dried over MgSO$_4$, filtered and evaporated to give a suspension. The suspension was filtered, washed with cold EtOAc (10 mL) and dried to give Boc—Arg(Tos)—N(Me)OMe (1.5 g, 70% yield). FAB—MS (M+H)$^+$=472

EXAMPLE 2

Preparation of Boc—Arg(Tos)—Thiazole

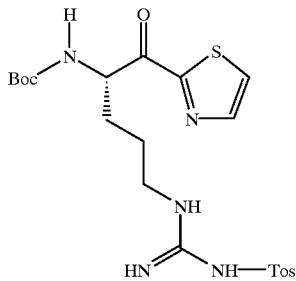

To a solution of thiazole (2.5 g, 29 mmol) in THF (25 mL) at −78° C. was added n-BuLi (1.6 M in hexane, 19 mL) dropwise. The mixture was stirred for 30 min. Then a solution of Boc—Arg(Tos)—N(Me)OMe (1.7 g, 3.6 mmol) in THF(50 mL) was added to the lithiothiazole mixture at −78° C. The solution was stirred for 2 h. 1 M HCl (30 mL) was added to the reaction mixture and warmed to room temperature. The mixture was extracted with EtOAc (100 mL). The organic layer was washed with sat. NaCl (30 mL), dried over MgSO$_4$, filtered and evaporated. The crude oily residue was purified by flash column over silica gel(50% EtOAc in CH$_2$Cl2) to give Boc—Arg(Tos)—Thiazole (1.5 g, 84% yield) as a white powder. DCl—MS(M+H)$^+$=496

EXAMPLE 3

Preparation of Boc—(D)—Arg(Cbz$_2$)—OSu

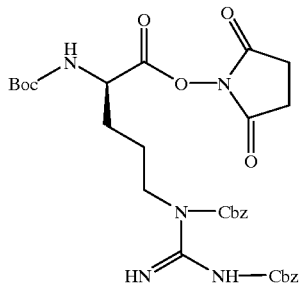

To a solution of Boc—(D)—Arg(Cbz$_2$)—OH ( 1 g, 1.8 mmol) in CH$_2$Cl$_2$ (10 mL) was added HOSu (466 mg, 4.06 mmol), DIEA (1 mL) and EDC (846 mg, 4.4 mmol). The solution was stirred for 48 h. The solvent was evaporated and residue was dissolved in EtOAc (50 mL) and water (10 mL). The separated organic layer was washed with sat. NaHCO$_3$ (10 mL), water (10 mL), 1 M HCl (10 mL) and sat. NaCl (3×10 mL). The organic layer was dried over MgSO$_4$, filtered and evaporated. The oily residue was either used directly in Example 4 without further purification or purified by flash column over silica gel (50% EtOAc in hexane) to give Boc—(D)—Arg(Cbz$_2$)—OSu (1 g, 85% yield).

EXAMPLE 4

Preparation of Boc—(D)—Arg(Cbz$_2$)—Gly—OH

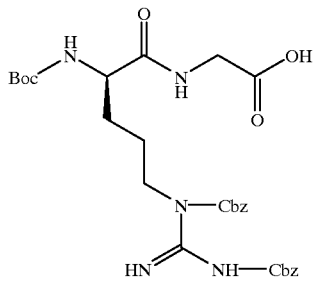

To a solution of Boc—(D)—Arg(Cbz$_2$)—OSu (1 g, 1.6 mmol) in dioxane (10 mL) was added a solution of Gly (300 mg, 4 mmol) and NaHCO3 (400 mg, 4.76 mmol) in water (10 mL). The solution was stirred for 24 h. Solvents were evaporated and residue was dissolved in a mixture of EtOAc (20 mL) and 1 N HCl (6 mL). The separated organic layer was washed with sat. NaCl (10 mL), dried over MgSO$_4$, filtered and evaporated to give a solid residue which was used directly without further purification. ES—MS (M+H)$^+$=600

EXAMPLE 5

Preparation of H—Arg(Tos)—Thiazole

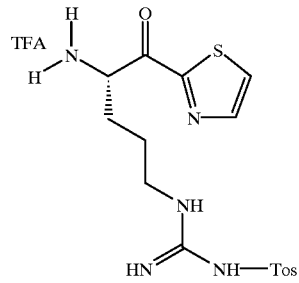

To a solution of Boc—Arg(Tos)—Thiazole (300 mg, 0.6 mmol) in CH$_2$Cl$_2$ (10 mL) at 0° C. was added TFA (10 mL). The solution was stirred at 0° C. for 2 h. The solvent and excess TFA were evaporated to an oily residue which was used directly without further purification in Example 6.

EXAMPLE 6

Preparation of Boc—(D)—Arg(Cbz$_2$)—Gly—Arg(Tos)—Thiazole

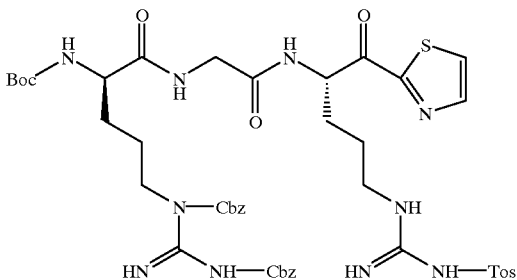

To a solution of Boc—Arg(Tos)—Thiazole (300 mg, 0.6 mmol) in CH$_2$Cl$_2$ (10 mL) at 0° C. was added TFA (10 mL). The solution was stirred at 0° C. for 2 h. The solvent and excess TFA were evaporated to an oily residue which was redissolved in CH$_2$Cl$_2$ (10 mL). The solution was cooled to 0° C., treated with DIEA (2 mL), Boc—(D)—Arg(Cbz$_2$)—Gly (400 mg, 0.67 mmol) and BOP (350 mg, 0.79 mmol). The solution was stirred at 0° C. for 2 h. Solvent was evaporated and residue was dissolved in EtOAc (50 mL). The organic solution was washed with sat. NaHCO$_3$ (10 mL), water (10 mL), 1 N HCl (10 mL) and sat. NaCl (10 mL). The organic layer was dried over MgSO$_4$, filtered and evaporated. The oily residue was purified by flash column over SiO$_2$ (EtOAc) to give Boc—(D)—Arg(Cbz$_2$)—Gly—Arg(Tos)—Thiazole (474 mg, 81% yield) as a powder. ES—MS (M+H)$^+$977

EXAMPLE 7

Preparation of H—(D)—Arg—Gly—Arg—Thiazole

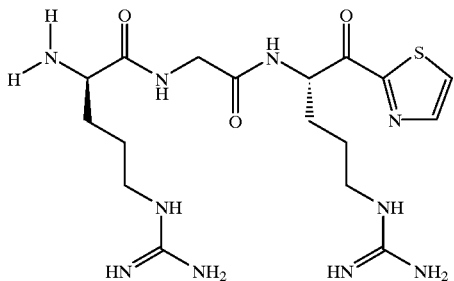

A 100 mg portion of Boc—(D)—Arg(Cbz$_2$)—Gly—Arg(Tos)—Thiazole, 1 mL of anisole and 4 drops of MeSEt were placed in HF-cleavage vessel and cooled under liquid N$_2$. HF (10 mL) was then condensed into the reaction mixture and stirred at 0° C. for 1.25 h. HF was removed under vacuum to give a gum-like residue which was titrated with 20 mL of 50% Et$_2$O-hexane and the organic wash removed by filtration. The gum residue was dissolved in 30 mL of 30% aq. HOAc and filtered through the above sintered funnel. The filtrate was lyophilized to give a powder which was purified by RP—HPLC to give 28 mg (60% yield) of (D)—Arg—Gly—Arg— thiazole. FAB—MS (M+H)$^+$= 455.2

EXAMPLE 8

Preparation of Boc—(D)—Arg(Tos)—Gly—OBn

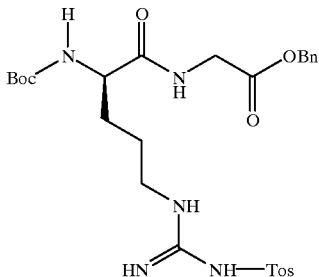

To a suspension of Boc—(D)—Arg(Tos)—OH (1 g, 2.34 mmol) in CH$_2$Cl$_2$ (10 mL) was added DIEA (1 mL) at 0° C. To the clear solution was added Gly—OBn.HCl (0.52 g, 2.58 mmol) and BOP (1.2 g, 2.8 mmol). The solution was stirred for 4 h at 0° C. Solvents were evaporated and residue was dissolved in a mixture of EtOAc (100 mL) and water (20 mL). The organic layer was washed with sat. NaHCO$_3$ (10 mL), water (10 mL), 1 N HCl (10 mL) and sat. NaCl (3×10 mL), dried with MgSO$_4$, filtered and evaporated. The solid residue was purified by column chromatography on silica gel (EtOAc) to give 1.12 g of the title compound as a powder. ES—MS (M+H)$^+$=576.3

EXAMPLE 9

Preparation of H—(D)—Arg(Tos)—Gly—OBn

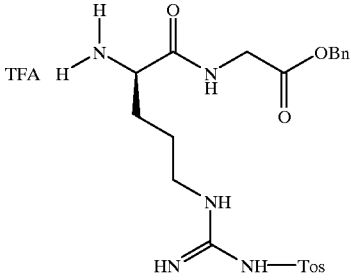

A 1 g portion of Boc—(D)—Arg(Tos)—Gly—OBn (1.74 mmol) was dissolved in 10 mL of CH$_2$Cl$_2$, cooled to 0° C. and treated with 10 mL of TFA. The solution was stirred at 0° C. for 3 h. Solvent and excess TFA were evaporated thoroughly to give the title compound as an oil which was used directly in Example 10.

EXAMPLE 10

Preparation of BnSO$_2$—(D)—Arg(Tos)—Gly—OBn

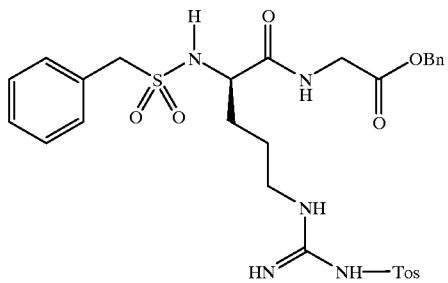

The oily residue of the compound of Example 9 was dissolved in 5 mL of DMF, cooled to 0° C. and neutralized with 1 mL of TEA. To the solution was added BnSO$_2$Cl (397 mg, 2.0 mmol) and the solution was stirred at 0° C. for 3 h and 25° C. for 3 h. DMF was removed and residue was dissolved in 100 mL of EtOAc and 20 mL of water. The organic layer was separated, washed with sat. NaHCO$_3$ (10 mL), water (10 mL), 1 N HCl (10 mL) and sat. NaCl (3×10 mL), dried with MgSO$_4$, filtered and evaporated. The solid residue was purified by column chromatography on silica gel (EtOAc) to give the title compound (328 mg, 30% yield) as a powder. ES—MS (M+H)$^+$630.5

EXAMPLE 11

Preparation of BnSO₂—(D)—Arg(Tos)—Gly—OH

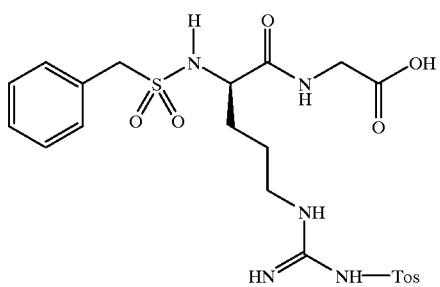

The compound of Example 10 (300 mg, 0.47 mmol) was dissolved in 10 mL of MeOH and then 10% Pd/C (150 mg) was added. The reaction was hydrogenated under normal pressure overnight, filtered through Celite, rinsed with MeOH (3×10 mL) and concentrated in vacuo to give the desired compound (242 mg, 84%) which was used without further purification. ES—MS (M+H)$^+$540.0

EXAMPLE 12

Preparation of BnSO₂—(D)—Arg(Tos)—Gly—Arg (Tos)—Thiazole

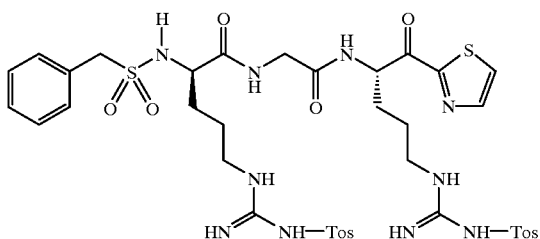

A 100 mg portion of the compound of Example 11 was coupled with 0.19 mmol of H—Arg(Tos)—thiazole (prepared following the procedure of Example 5) following the procedure as described in Example 6. RP—HPLC purification gave the title compound (110 mg, 63% yield). FAB—MS (M+H)$^+$917.8

EXAMPLE 13

Preparation of BnSO₂—(D)—Arg—Gly—Arg— Thiazole

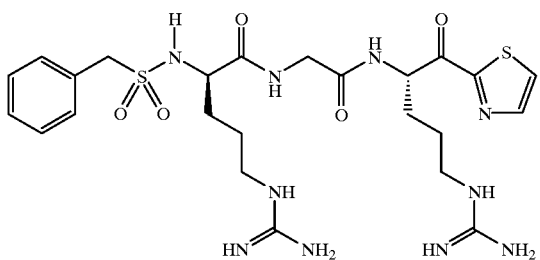

The compound of Example 13 was HF-cleaved according to the procedures described in Example 7 and purified by reversed phase HPLC to give the title compound as a powder (35 mg, 47% yield). ES—MS (M+H)$^+$=609.6

EXAMPLE 14

Evaluation of the compounds of this invention is guided by in vitro protease activity assays (see below) and in vivo studies to evaluate antithrombotic efficacy, and effects on hemostasis and hematological parameters (see Example 15 below).

The compounds of the present invention are dissolved in buffer to give solutions containing concentrations such that assay concentrations range from 0 to 100 μM. In the assays for thrombin, prothrombinase and factor Xa, a synthetic chromogenic substrate is added to a solution containing test compound and the enzyme of interest and the residual catalytic activity of that enzyme is determined spectrophotometrically. The $IC_{50}$ of a compound is determined from the substrate turnover. The $IC_{50}$ is the concentration of test compound giving 50% inhibition of the substrate turnover. The compounds of the present invention desirably have an $IC_{50}$ of less than 500 nM in the factor Xa assay, preferably less than 200 nM, and more preferred compounds have an $IC_{50}$ of about 100 nM or less in the factor Xa assay. The compounds of the present invention desirably have an $IC_{50}$ of less than 4.0 μM in the prothrombinase assay, preferably less than 200 nM, and more preferred compounds have an $IC_{50}$ of about 10 nM or less in the prothrombinase assay. The compounds of the present invention desirably have an $IC_{50}$ of greater than 1.0 μM in the thrombin assay, preferably greater than 10.0 μM, and more preferred compounds have an $IC_{50}$ of greater than 100.0 μM in the thrombin assay.

Amidolytic Assays for determining protease inhibition activity

The factor Xa and thrombin assays were performed at room temperature, in 0.02 M Tris-HCl buffer, pH 7.5, containing 0.15 M NaCl. The rates of hydrolysis of the paranitroanilide substrate S-2765 (Chromogenix) for factor Xa, and the substrate Chromozym TH (Boehringer Mannheim) for thrombin following preincubation of the enzyme with inhibitor for 5 minutes at room temperature, and were determined using the Softmax 96-well plate reader (Molecular Devices), monitored at 405 nm to measure the time dependent appearance of p-nitroaniline.

The prothrombinase inhibition assay was performed in a plasma free system with modifications to the method described by Sinha, U. et al., Thromb. Res., , 427–436 (1994). Specifically, the activity of the prothrombinase complex was determined by measuring the time course of thrombin generation using the p-nitroanilide substrate Chromozym TH. The assay consists of preincubation ( 5 minutes) of selected compounds to be tested as inhibitors with the complex formed from factor Xa (0.5 nM), factor Va (2 nM), phosphatidyl serine:phosphatidyl choline (25:75, 20 μM) in 20 mM Tris-HCl buffer, pH 7.5, containing 0.15 M NaCl, 5 mM CaCl₂ and 0.1% bovine serum albumin. Aliquots from the complex-inhibitor mixture were added to prothrombin (1 nM) and Chromozym TH (0.1 mM). The rate of substrate cleavage was monitored at 405 nm for two minutes. Eight different concentrations of inhibitor were assayed in duplicate. A standard curve of thrombin generation by an equivalent amount of untreated complex was used for determination of percent inhibition.

EXAMPLE 15

A series of studies were accomplished in rabbits to evaluate the antithrombotic efficacy, and effects on hemostasis and hematological parameters of the compound (D)—Arg—Gly—Arg—thiazole.

Antithrombotic Efficacy in a Rabbit Model of Venous Thrombosis

A rabbit deep vein thrombosis model as described by Hollenbach, S. et al., Thromb. Haemost. 71, 357–362 (1994), was used to determine the in-vivo antithrombotic activity of the test compounds. Rabbits were anesthetized with I. M. injections of Ketamine, Xylazine, and Acepromazine cocktail. A standardized protocol consisted of insertion of a thrombogenic cotton thread and copper wire apparatus into the abdominal vena cava of the anesthetized rabbit. A non-occlusive thrombus was allowed to develop in the central venous circulation and inhibition of thrombus growth was used as a measure of the antithrombotic activity of the studied compounds. Test agents or control saline were administered through a marginal ear vein catheter. A femoral vein catheter was used for blood sampling prior to and during steady state infusion of test compound. Initiation of thrombus formation begins immediately after advancement of the cotton thread apparatus into the central venous circulation. Test compounds were administered from time= 30 min to time=150 min at which the experiment was terminated. The rabbits were euthanized and the thrombus excised by surgical dissection and characterized by weight and histology. Blood samples were analyzed for changes in hematological and coagulation parameters.

Effects of (D—)—Arg—Gly—Arg—thiazole in Rabbit Venous Thrombosis model

Administration of (D)—Arg—Gly—Arg—thiazole in the rabbit venous thrombosis model demonstrated antithrombotic efficacy at the higher doses evaluated. There was no significant effect of the compound on the aPTT and PT prolongation with the highest dose (100 $\mu$g/kg+2.57 $\mu$g/kg/min)(see Table 2). (D)—Arg—Gly—Arg—thiazole had no significant effects on hematological parameters as compared to saline controls (see Table 3).

TABLE 2

ANTITHROMBOTIC EFFECTS OF (D)-Arg-Gly-Arg-thiazole IN RABBITS

| Dose Regimen ($\mu$g/kg + $\mu$g/kg/min) | n# | % Inhibition of Thrombosis | fold increase over baseline aPTT | PT |
|---|---|---|---|---|
| saline control | 6 | 0.0 | 0.96 ± 0.01 | 1.00 ± 0.00 |
| 50 + 1.28 | 6 | -7.84 | 1.00 ± 0.03 | 1.00 ± 0.00 |
| 75 + 1.93 | 5 | 42.95 | 1.02 ± 0.03 | 1.00 ± 0.00 |
| 100 + 2.57 | 6 | 117.72 | 1.08 ± 0.02 | 0.83 ± 0.00 |

All measurements are an average of all samples after steady state administration of vehicle or (D)—Arg—G[y\]MArg—thiazole. Values are expressed as mean±SD.

TABLE 3

EFFECTS OF (D)-Arg-Gly-Arg-thiazole ON HEMATOLOGICAL PARAMETERS

| Dose Regimen ($\mu$g/kg + $\mu$g/kg/min) | n# | RBC x $10^6/\mu$L | WBC x $10^3/\mu$L | PLT x $10^3/\mu$L | Hct % |
|---|---|---|---|---|---|
| saline control | 6 | 5.96 ± 0.66 | 3.38 ± 0.83 | 338 ± 77 | 35.2 ± 2.81 |
| 50 + 1.28 | 6 | 5.66 ± 0.25 | 3.70 ± 0.50 | 349 ± 75 | 36.9 ± 3.90 |
| 75 + 1.93 | 5 | 5.74 ± 0.42 | 4.23 ± 0.99 | 413 ± 64 | 35.3 ± 3.01 |
| 100 + 2.57 | 6 | 6.08 ± 0.42 | 4.15 ± 0.52 | 439 ± 61 | 35.5 ± 1.01 |

All measurements are an average of samples after steady state administration of vehicle or (D)—Arg—GNy—Arg—thiazole. Values are mean±SD.

What is claimed is:
1. A compound having the formula:

[chemical structure]

or

[chemical structure]

wherein.

m is 0, 1, 2, 3, or 4;

n is 0, 1, 2, 3, or 4;

Y is selected from the group consisting of NH, S, O, $CH_2$, CH—OH, $CH_2CH_2$, and C=0;

A is piperdinyl, pyrrolidinyl, cyclopropyl, cyclobutyl, cyclopentyl, cyclohexyl, phenyl, $C_{3-6}$heteroaryl, or is absent;

$R_1$ is H or $C_{1-3}$alkyl;

J is O or $H_2$;

$R_2$ is H or $C_{1-3}$alkyl;

D is selected from the group consisting of N, CH, $NCH_2$, $NCH_2CH_2$, and $CHCH_2$;

$R_3$ is H or $C_{1-3}$allyl;

E is O or $H_2$;

$R_4$ is H or $CH_3$;

M is N, NH, N—$CH_3$, O, S, SO, $SO_2$, $CH_2$ or is absent;

Q is piperdinyl, pyrrolidynyl, $C_{3-8}$cycloalkyl, naphthyl, pyridyl, phenyl, phenyl substituted with one, two or three substituents selected from the group consisting of loweralkoxy, loweralkyl, lower alkylamino, hydroxy, halogen, cyano, hydroxyl, mercapto, nitro, thioalkoxy, carboxaldehyde, carboxyl, carboalkoxy and carboxamide, or Q is absent;

G is selected from the group consisting of N, CH, and H;

$R_5$ is H or $C_{1-3}$alkyl or is absent if G is H;

$R_6$ is H or $CH_3$;

U is selected from a group consisting of

[chemical structures]

where n is an integer from 0 to 4; $R_7$ and $R_8$ are independently selected from a group consisting of H, $C_{1-10}$alkyl, aryl, arylalkyl, halogen, nitro, an amino group of formula —$NR_9R_{10}$, an acylamino group of formula —NHCOR$_{11}$, hydroxy, an acyloxy group of formula —OCOR$_{12}$, C$_{1-4}$alkyloxy, C$_{1-4}$alkyl, trifluoromethyl, carboxy, cyano, phenyl, aromatic heterocyclic group, C$_{1-4}$alkyloxycarbonyl, an aminocarbonyl group of formula CONR$_{13}$R$_{14}$, sulfo, and sulfonamido of formula SO$_2$NR$_{15}$R$_{16}$ and C$_{1-6}$hydroxyalkyl, and wherein R$_9$, R$_{10}$, R$_{11}$, R$_{12}$, R$_{13}$, R$_{14}$, R$_{15}$, R$_{16}$ are the same or different and are H, C$_{1-4}$ alkyl, C$_{1-3}$arylalkyl or aryl, and if M is absent, U is:

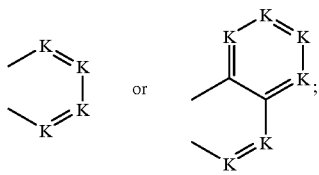

K is C or N;

W is H, arylacyl, heteroarylacyl, arylC$_{1-3}$alkylsulfonyl, arylsulfonyl, substituted arylsulfonyl, arylC$_{1-4}$ alkenylsulfonyl, C$_{1-4}$alkylsulfonyl, heteroaryl-C$_{1-3}$ alkylsulfonyl, heteroarylsulfonyl, aryloxycarbonyl, C$_{1-4}$alkyloxycarbonyl, arylC$_{1-3}$alkyloxycarbonyl, arylaminocarbonyl, C$_{1-6}$alkylaminocarbonyl, arylC$_{1-3}$alkylaminocarbonyl, HOOC—CO$_{1-3}$alkylcarbonyl, or is absent if G is H;

X is selected from the group consisting of H, C$_{1-3}$alkyl, NR'R", NH—C(NR'R")=NH, NH—C(NHR')=NR", NH—C(R')=NR", S—C(NR'R")=NH, S—C(NHR')=NR", C(NR'R")=NH, C(NHR')=NR" and CR'=NR"; where: R',R" are the same or different and are H, C$_{1-6}$alkyl, C$_{1-3}$arylalkyl, aryl or where R'R" forms a cyclic ring containing (CH)p where p is an integer from 2 to 5;

Z is selected from the group consisting of H, C$_{1-3}$alkyl, NR'R", NH—C(NR'R")=NH, NH—C(NHR')=NR", NH—C(R')=NR", S—C(NR'R")=NH, S—C(NHR')=NR", C(NR'R")=NH, C(NHR')=NR" and CR'=NR"; where: R',R" are the same or different and are H, C$_{1-6}$alkyl, C$_{1-3}$arylalkyl, aryl or where R'R" forms a cyclic ring containing (CH$_2$)$_p$ where p is an integer from 2 to 5;

wherein said compound is a selective Factor Xa inhibitor and has an IC$_{50}$ of less than about 0.5 $\mu$M for Factor Xa;

or a pharmaceutically acceptable isomer, salt, hydrate, or solvate thereof.

2. The compound of claim 1, having the formula:

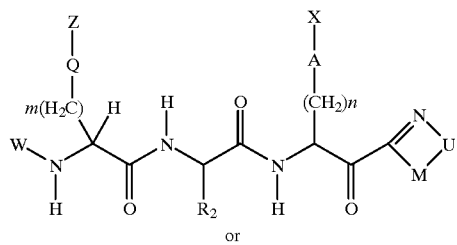

or

-continued

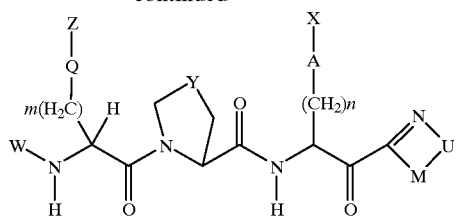

wherein:

m is 0, 1, 2, 3, or 4;

n is 0, 1, 2, 3, or 4;

Y is selected from the group consisting of NH, S, O, CH$_2$, CH—OH, and CH$_2$CH$_2$;

A is piperdinyl, pyrrolidinyl, cyclopropyl, cyclobutyl, cyclopentyl, cyclohexyl, phenyl C$_{3-6}$heteroaryl, or is absent;

M is NH, N—CH$_3$, O, S, SO, SO$_2$, CH$_2$ or is absent;

Q is piperdinyl, pyrrolidinyl, C$_{3-8}$ cycloalkyl, phenyl, substituted phenyl, naphthyl, pyridyl, or is absent U is selected from a group consisting of

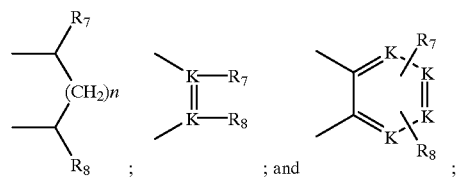

where n=0–4; R$_7$ and R$_8$ are independently selected from a group consisting of H, C$_{1-10}$alkyl, aryl arylalkyl, halogen, nitro, an amino group of formula —NR$_9$R$_{10}$, an acylamino group of formula —NHCOR$_{11}$, hydroxy, an acyloxy group of formula —OCOR$_{12}$, C$_{1-4}$alkyloxy, C$_{1-4}$alkyl, trifluoromethyl, carboxy, cyano, phenyl, aromatic heterocyclic group, C$_{1-4}$alkyloxycarbonyl, an aminocarbonyl group of formula CONR$_{1-4}$R$_{1-4}$, sulfo, and sulfonamido of formula SO$_2$NR$_{15}$R$_{16}$ and C$_{1-6}$ hydroxyalkyl; wherein R$_9$, R$_{10}$, R$_{11}$, R$_{12}$, R$_{13}$, R$_{14}$, R$_{15}$, R$_{16}$, are the same or different and are H, C$_{1-6}$ alkyl, C$_{1-3}$arylalkyl or aryl; and if M is absent U is:

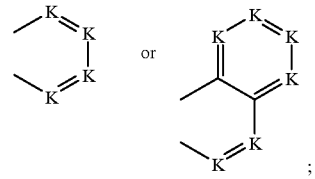

K is C or N;

W is H, arylacyl, heteroarylacyl, arylC$_{1-3}$alkylsulfonyl, arylsulfonyl, substituted arylsulfonyl, arylC$_{1-4}$alkenylsulfonyl, C$_{1-8}$alkylsulfonyl, heteroarylC$_{1-3}$alkylsulfonyl, heteroarylsulfonyl, aryloxycarbonyl, C$_{1-6}$alkyloxycarbonyl, arylC$_{1-3}$alkyloxycarbonyl, arylaminocarbonyl, C$_{1-6}$alkylaminocarbonyl, arylC$_{1-3}$alkylaminocarbonyl, HOOC—C$_{0-3}$alkylcarbonyl, or is absent if G is H;

X is selected from the group consisting of NR'R", NH—C (NR'R")=NH, NH—C(NHR')=NR", NH—C(R')

=NR", S—C(NR'R")—NH, S—C(NHR')—NR", C(NR'R")=NH, C(NHR')=NR" and CR'=NR"; where R'R" are the same or different and are H, $C_{1-6}$alkyl, $C_{1-3}$arylalkyl, aryl or where R'R" forms a cyclic ring containing $(CH_2)p$ where p is an integer from 2 to 5;

Z is selected from the group consisting of NR'R", NH—C(NR'R")=NH, NH—C(NHR')=NR", NH—C(R')=NR", S—C(NR'R")=NH, S—C(NHR')=NR", C(NR'R")=NH, C(NHR')=NR" and CR'=NR"; where: R'R" are the same or different and are H, $C_{1-6}$alkyl, aryl or where R'R" forms a cyclic ring containing $(CH_2)p$ where p is an integer from 2 to 5;

or a pharmaceutically acceptable isomer, salt, hydrate, or solvate thereof.

3. The compound of claim 1, having an $IC_{50}$ for Factor Xa of less than about 200 nM.

4. The compound of claim 1, having an $IC_{50}$ for pro-thrombinase of less than about 2.0 μM.

5. The compound of claim 1, having an $IC_{50}$ for thrombin of greater than about 1.0 μm.

6. A compound selected from a group consisting of:

$PhCH_2CH_2$—$SO_2$—(D)—Arg—Gly—Arg—Thiazole
$C_6H_{11}CH_2CH_2SO_2$—(D)—Arg—Gly—Arg—Thiazole
$Me_3C$—$C_6H_4SO_2$—(D)—Arg—Gly—Arg—Thiazole
$C_{10}H_7SO_2$—(D)—Arg—Gly—Arg—Thiazole
$Me_3SiCH_2CH_2CH_2SO_2$—(D)—Arg—Gly—Arg—Thiazole
H—D—Arg—Gly—Arg—Thiazole
$BnSO_2$—(D)—Arg—Gly—Arg—Thiazole
$BnSO_2$—(D)—4-Apa—Gly—Arg—Thiazole
$BnSO_2$—(D)—4-Gpa—Gly—Arg—Thiazole
$BnSO_2$—(D)—4-Acg—Gly—Arg—Thiazole
$BnSO_2$—(D)—homo—Lys—Gly—Arg—Thiazole
$BnSO_2$—(D)—Arg—Sar—Arg—Thiazole
$BnSO_2$—(D)—Arg—Pro—Arg—Thiazole
$BnSO_2$—(D)—Arg—Gly—4-Acg—Thiazole
$BnSO_2$—(D)—Arg—Gly—(3-$NH_2$—Phe)—Thiazole
$BnSO_2$—(D)—Arg—Gly—(4-$NH_2$—Phe)—Thiazole
$BnSO_2$—(D)—Arg—Gly—3-Gpa—Thiazole
$BnSO_2$—(D)—Arg—Gly—4-Gpa—Thiazole
Boc—D—(2,3-Dap)—Gly—Arg—Thiazole
Boc—D—(2,4-Dab)—Gly—Arg—Thiazole
g—Abu—Gly—Arg—Thiazole
Boc—D—Orn—Gly—Arg—Thiazole
Boc—D—homoLys—Gly—Arg—Thiazole
Boc—Bag—Gly—Arg—Thiazole
Boc—D—4-Gpa—Gly—Arg—Thiazole
Boc—D—3-Gpa—Gly—Arg—Thiazole
Boc-D4-Apa—Gly—Arg—Thiazole
Boc—D—3-Apa—Gly—Arg—Thiazole
Boc—D—4-Acg—Gly—Arg—Thiazole
Boc—D—(4-$NH_2$Phe)—Gly—Arg—Thiazole
Boc—D—(3-$NH_2$Phe)—Gly—Arg—Thiazole
$BnSO_2$—D—(2,3-Dap)—Gly—Arg—Thiazole
$BnSO_2$—D—(2,4-Dab)—Gly—Arg—Thiazole
$BnSO_2$—D—Orn—Gly—Arg—Thiazole
$BnSO_2$—Bag—Gly—Arg—Thiazole
$BnSO_2$—D—3-Gpa—Gly—Arg—Thazole
$BnSO_2$—D—3-Apa—Gly—Arg—Thiazole
$BnSO_2$—D—(4-$NH_2$Phe)—Gly—Arg—Thiazole
$BnSO_2$—D—(3-$NH_2$Phe)—Gly—Arg—Thiazole
$BnSO_2$—D—(2,3-Dap)—Gly—Arg—Benzothiazole
$BnSO_2$—D—(2,4-Dab)—Gly—Arg—Benzothiazole
$BnSO_2$—D—Orn—Gly—Arg—Benzothiazole
$BnSO_2$—Bag—Gly—Arg—Benzothiazole
$BnSO_2$-D4-Gpa—Gly—Arg—Benzothiazole
$BnSO_2$—D—3-Gpa—Gly—Arg—Benzothiazole
$BnSO_2$—D—4-Apa—Gly—Arg—Benzothiazole
$BnSO_2$—D—3-Apa—Gly—Arg—Benzothiazole
$BnSO_2$—D—4-Acg—Gly—Arg—Benzothiazole
$BnSO_2$—D—(4-$NH_2$Phe)—Gly—Arg—Benzothiazole
$BnSO_2$—D—(3-$NH_2$Phe)—Gly—Arg—Benzothiazole
$BnSO_2$—D—Arg—Gly—(2,4-Dab)-Benzothiazole
$BnSO_2$—D—Arg—Gly—(homoLys)—Benzothiazole
$BnSO_2$—D—Arg—Gly—(4-Gpa)—Benzothiazole
$BnSO_2$—D—Arg—Gly—(3-Gpa)—Benzothiazole
$BnSO_2$—D—Arg—Gly—(4-Apa)—Benzothiazole
$BnSO_2$—D—Arg—Gly—(3-Apa)—Benzothiazole
$BnSO_2$—D—Arg—Gly—(4-$NH_2$Phe)—Benzothiazole
$BnSO_2$—D—Arg—Gly—(3-$NH_2$Phe)—Benzothiazole
$Me_3SiCH_2CH_2CH_2SO_2$—(D)—Arg—Gly—Arg—Benzothiazole
$BnSO_2$—(D)—homo—Lys—Gly—Arg—Benzothiazole
$BnSO_2$—(D)—homoLys—Gly—Arg—Benzoxazole
$PhCH_2CH_2$—$SO_2$—(D)—Arg—Gly—Arg—Benzothiazole
$BnSO_2$—(D)—Arg—Sar—Arg—Benzothiazole
$BnSO_2$—(D)—Arg—Pro—Arg—Benzothiazole
$BnSO_2$—(D)—Arg—GlyA—Acg—Benzothiazole
$BnSO_2$—(D)—Arg—Gly—Arg—Benzothiazole
$PhCH_2CH_2SO_2$—(D)—Arg—Gly—4-Acg—Benzoffiiazole
$BnSO_2$—(D)—Arg—Gly—Arg—Oxazole
Boc—D—(2,3—Dap)—Gly—Arg—Oxazole
Boc—D—(2,4—Dab)—Gly—Arg—Oxazole
g—Abu—Gly—Arg—Oxazole
Boc—D—Orn—Gly—Arg—Oxazole
Boc—D—homoLys—Gly—Arg—Oxazole
Boc—Bag—Gly—Arg—Oxazole
Boc—D4-Gpa—Gly—Arg—Oxazole
Boc—D—3-Gpa—Gly—Arg—Oxazole
Boc—D—4-Apa—Gly—Arg—Oxazole
Boc—D—3-Apa—Gly—Arg—Oxazole
Boc—D—4-Acg—Gly—Arg—Oxazole
Boc—D—(4-$NH_2$Phe)—Gly—Arg—Oxazole
Boc—D—(3-$NH_2$Phe)—Gly—Arg—Oxazole
$BnSO_2$—D—(2,3-Dap)—Gly—Arg—Oxazole
$BnSO_2$—D—(2,4-Dab)—Gly—Arg—Oxazole
$BnSO_2$—D—Orn—Gly—Arg—Oxazole
$BnSO_2$—Bag—Gly—Arg—Oxazole
$BnSO_2$—D—4-Gpa—Gly—Arg—Oxazole
$BnSO_2$—D—3-Gpa—Gly—Arg—Oxazole
$BnSO_2$—D—4-Apa—Gly—Arg—Oxazole
$BnSO_2$—D—3-Apa—Gly—Arg—Oxazole
$BnSO_2$—D—4-Acg—Gly—Arg—Oxazole BnSO₂—D—(4-NH₂Phe)—Gly—Arg—Oxazole
BnSO₂—D—(3-NH₂Phe)—Gly—Arg—Oxazole
BnSO₂—D—Arg—Gly—(2,4-Dab)—Oxazole
BnSO₂—D—Arg—Gly—(homoLys)—Oxazole
BnSO₂—D—Arg—Gly—(4-Gpa)—Oxazole
BnSO₂—D—Arg—Gly—(3-Gpa)—Oxazole
BnSO₂—D—Arg—Gly—(4-Apa)—Oxazole
BnSO₂—D—Arg—Gly—(3-Apa)—Oxazole
BnSO₂—D—Arg—Gly—(4-NH₂Phe)—Oxazole
BnSO₂—D—Arg—Gly—(3-NH₂Phe)—Oxazole
BnSO₂—D—(2,3-Dap)—Gly—Arg—Benzoxazole
BnSO₂—D—(2,4-Dab)—Gly—Arg—Benzoxazole
BnSO₂—D—Orn—Gly—Arg—Benzoxazole
BnSO₂—Bag—Gly—Arg—Benzoxazole
BnSO₂—D—4-Gpa—Gly—Arg—Benzoxazole
BnSO₂—D—3-Gpa—Gly—Arg—Benzoxazole
BnSO₂—D—4-Apa—Gly—Arg—Benzoxazole
BnSO₂—D—3-Apa—Gly—Arg—Benzoxazole
BnSO₂—D—4-Acg—Gly—Arg—Benzoxazole
BnSO₂—D—(4-NH₂Phe)—Gly—Arg—Benzoxazole
BnSO₂—D—(3-NH₂Phe)—Gly—Arg—Benzoxazole
BnSO₂—D—Arg—Gly—(2,4-Dab)—Benzoxazole
BnSO₂—D—Arg—Gly—(homoLys)—Benzoxazole
BnSO₂—D—Arg—Gly—(4-Gpa)—Benzoxazole
BnSO₂—D—Arg—Gly—(3-Gpa)—Benzoxazole
BnSO₂—D—Arg—Gly—(4-Apa)—Benzoxazole
BnSO₂—D—Arg—Gly—(3-Apa)—Benzoxazole
BnSO₂—D—Arg—Gly—(4-NH₂Phe)—Benzoxazole
BnSO₂—D—Arg—Gly—(3-NH₂Phe)—Benzoxazole
Me₃SiCH₂CH₂CH₂SO₂—(D)—Arg—Gly—Arg—Benzoxazole
BnSO₂—(D)—homo—Lys—Gly—Arg—Benzoxazole
PhCH₂CH₂—SO₂—(D)—Arg—Gly—Arg—Benzoxazole
BnSO₂—(D)—Arg—Sar—Arg—Benzoxazole
BnSO₂—(D)—Arg—Pro—Arg—Benzoxazole
BnSO₂—(D)—Arg—Gly—4-Acg—Benzoxazole
BnSO₂—(D)—Arg—Gly—Arg—Benzoxazole
PhCH₂CH₂SO₂—(D)—Arg—Gly+Acg—Benzoxazole
BnSO₂—(D)—Arg—Gly—Ar g—Benzoxazole
PhCH₂CH₂—SO₂—(D)—Arg—Gly—Arg—Benzoxazole
PhCH₂CH₂—SO₂—(D)—Arg—Gly—4-Acg—Benzoxazole
Me₃SiCH₂CH₂CH₂SO₂—(D)—Arg—Gly—Arg—Benzoxazole
BnSO₂—(D)—Arg—Gly—Arg—Oxazoline
Boc—D—(2,3-Dap)—Gly—Arg—Oxazoline
Boc—D—(2,4-Dab)—Gly—Arg—Oxazoline
g —Abu—Gly—Arg—Oxazoline
Boc—D—Orn—Gly—Arg—Oxazoline
Boc—D—homoLys—Gly—Arg—Oxazoline
Boc—Bag—Gly—Arg—Oxazoline
Boc—D—4-Gpa—Gly—Arg—Oxazoline
Boc—D—3-Gpa—Gly—Arg—Oxazoline
Boc—D—4-Apa—Gly—Arg—Oxazoline
Boc—D—3-Apa—Gly—Arg—Oxazoline
Boc—D—4-Acg—Gly—Arg—Oxazoline
Boc—D—(4-NH₂Phe)—Gly—Arg—Oxazoline
Boc—D—(3-NH₂Phe)—Gly—Arg—Oxazoline
BnSO₂—D—(2,3-Dap)—Gly—Arg—Oxazoline
BnSO₂—D—(2,4-Dab)—Gly—Arg—Oxazoline
BnSO₂—D—Orn—Gly—Arg—Oxazoline
BnSO₂—Bag—Gly—Arg—Oxazoline
BnSO₂—D—4-Gpa—Gly—Arg—Oxazoline
BnSO₂—D—3-Gpa—Gly—Arg—Oxazoline
BnSO₂—D4-Apa—Gly—Arg—Oxazoline
BnSO₂—D—3-Apa—Gly—Arg—Oxazoline
BnSO₂—D—4-Acg—Gly—Arg—Oxazoline
BnSO₂—D—(4-NH₂Phe)—Gly—Arg—Oxazoline
BnSO₂—D—(3-NH₂Phe)—Gly—Arg—Oxazoline
BnSO₂—D—Arg—Gly—(2,4-Dab)—Oxazoline
BnSO₂—D—Arg—Gly—(homoLys)—Oxazoline
BnSO₂—D—Arg—Gly—(4-Gpa)—Oxazoline
BnSO₂—D—Arg—Gly—(3-Gpa)—Oxazoline
BnSO₂—D—Arg—Gly—(4-Apa)—Oxazoline
BnSO₂—D—Arg—Gly—(3-Apa)—Oxazoline
BnSO₂—D—Arg—Gly—(4-NH₂Phe)—Oxazoline
BnSO₂—D—Arg—Gly—(3-NH₂Phe)—Oxazoline
BnSO₂—(D)—Arg—Gly—Arg—Imidazole
BnSO₂—(D)—Arg—Gly—Arg—Pyridine
BnSO₂—(D)—Arg—Gly—Arg—2-(1-methyl-tetrazole) and
BnSO₂—(D)—Arg—Gly—Arg—2-(4-methyl-tetrazole).

7. The compound of claim 6, wherein said compound is H—D—Arg—Gly—Arg—thiazole.

8. The compound of claim 6, wherein said compound is BnSO₂—(D)—Arg—Gly—Arg—thiazole.

9. The compound of claim 1, having the formula:

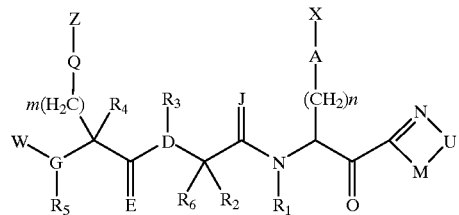

wherein:

A is piperdinyl, pyrollidinyl, cyclopentyl, cyclohexyl, phenyl, $C_{3-8}$ heteroaryl or is absent;

D is N, CH or NCH₂;

M is NH, O, S, CH₂ or is absent;

Q is piperdinyl, pyrrolidinyl, $C_{3-8}$ cycloalkyl, phenyl, substituted phenyl or is absent;

U is selected from the group consisting of

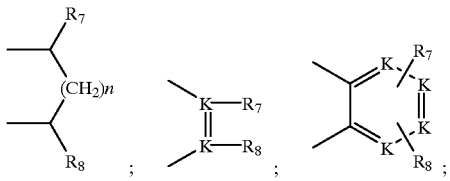

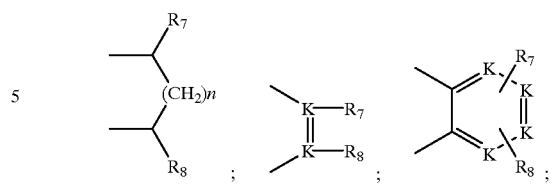

where n is 0–2; $R_7$ and $R_8$ are independently selected from the group consisting of H, $C_{1-10}$aryl, arylalkyl, halogen, nitro, trifluoromethyl, carboxy, cyano; and if M is absent:

wherein n is 0–2, $R_7$ and $R_8$ are independently selected from the group consisting of H, $C_{1-10}$ alkyl, aryl, arylalkyl, halogen, nitro, trifluoromethyl, carboxy, cyano; and if M is absent:

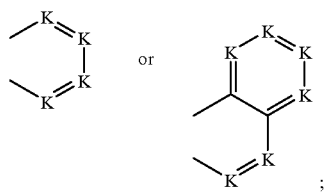

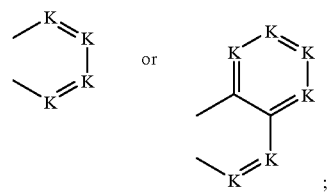

and where K is C or N.

K is C or N;

16. The compound of claim 1 wherein W is aryl$C_{1-3}$alkylsulfonyl, arylsulfonyl, substituted arylsulfonyl, aryl$C_{1-4}$alkenylsulfonyl, $C_{1-8}$alkylsulfonyl, heteroaryl$C_{1-3}$alkylsulfonyl, heteroarylsulfonyl, $C_{1-6}$alkyloxycarbonyl, aryl$C_{1-3}$alkyloxycarbonyl, or is absent if G is H.

W is aryl$C_{1-3}$alkylsulfonyl, arylsulfonyl, substituted arylsulfonyl, aryl$C_{1-4}$alkenylsulfonyl, $C_{1-8}$alkylsulfonyl, heteroaryl$C_{1-3}$alkylsulfonyl, heteroarylsulfonyl, $C_{1-6}$alkyloxycarbonyl, aryl$C_{1-3}$alkyloxycarbonyl, or is absent if G is H;

17. The compound of claim 1 wherein X is selected from the group consisting of NR'R", NH—C(NR'R")=NH, NH—C(NHR')=NR", NH—C(R')=NR", S—C(NR'R")=NH, S—C(NHR')=NR", C(NR'R")=NH and C(NHR')=NR"; where: R',R" are the same or different and are H or $C_{1-6}$alkyl.

X is selected from the group consisting of NR'R", NH—C(NR'R")=NH, NH—C(NHR')=NR", NH—C(R')=NR", S—C(NR'R")=NH, S—C(NHR')=NR", C(NR'R")=NH and C(NHR')=NR"; where: R',R" are the same or different and are H or $C_{1-6}$alkyl;

18. The compound of claim 1 wherein Z is selected from the group consisting of NH—C(NR'R")=NH, NH—C(NHR')=NR", NH—C(R')=NR", S—C(NR'R")=NH, S—C(NHR')=NR", C(NR'R")=NH and C(NHR')=NR"; where R',R" are the same or different and are H or $C_{1-6}$alkyl.

Z is selected from the group consisting of NH—C(NR'R")=NH, NH—C(NHR')=NR", NH—C(R')=NR", S—C(NR'R")=NH, S—C(NHR')=NR", C(NR'R")=NH and C(NHR')=NR"; where R',R" are the same or different and are H or $C_{1-6}$alkyl.

19. The compound of claim 1 wherein G is N.
20. The compound of claim 1 wherein D is N.
21. The compound of claim 1 wherein E is O.
22. The compound of claim 1 wherein J is O.
23. The compound of claim 1 wherein $R_1$ is H.
24. The compound of claim 1 wherein $R_3$ is H.
25. The compound of claim 1 wherein $R_4$ is H.
26. The compound of claim 1 wherein $R_5$ is H.
27. The compound of claim 1 wherein $R_6$ is H.
28. The compound of claim 1 wherein M is S and U is 10. The compound of claim 1 wherein Y is S, O, $CH_2$ or $CH_2CH_2$.

11. The compound of claim 1 wherein A is piperdinyl, pyrrolidinyl, cyclopentyl, cyclohexyl, phenyl, $C_{3-6}$heteroaryl or is absent.

12. The compound of claim 1 wherein D is N, CH or $NCH_2$.

13. The compound of claim 1 wherein M is NH, O, S, $CH_2$ or is absent.

14. The compound of claim 1 wherein Q is piperdinyl, pyrrolidinyl, $C_{3-8}$cycloalkyl, phenyl, substituted phenyl or is absent.

15. The compound of claim 1 wherein U is selected from the group consisting of

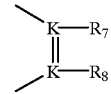

where K is C and $R_7$ and $R_8$ are H.

29. The compound of claim 1 wherein M is S and U is

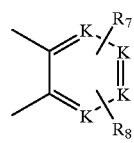

where K is C and $R_7$ and $R_8$ are H.

30. The compound of claim 1 wherein M is O and U is

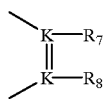

where K is C and $R_7$ and $R_8$ are H.

31. The compound of claim 1 wherein M is O and U is

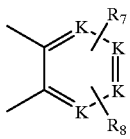

where K is C and $R_7$ and $R_8$ are H.

32. The compound of claim 1 wherein M is O and U is

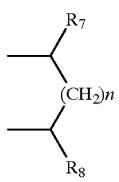

where n is O and $R_7$ and $R_8$ are H.

33. The compound of claim 1 wherein M is NH and U is

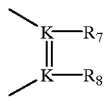

where K is C and $R_7$ and $R_8$ are H.

34. The compound of claim 1 wherein M is absent and U is

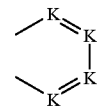

where K is C and $R_7$ and $R_8$ are H.

35. The compound of claim 1 wherein M is N—$CH_3$ and U is

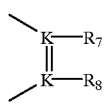

where K is N and $R_7$ and $R_8$ are H.

36. The compound of claim 1 wherein M is N and U is

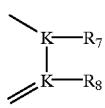

where K is N, $R_7$ is —$CH_3$ and $R_8$ is H.

37. The compound of claim 1, having an $IC_{50}$ for prothrombinase of less than about 4.0 $\mu$M.

38. The compound of claim 5, having an $IC_{50}$ for thrombin of greater than about 10.0 $\mu$M.

39. A compound having the formula:

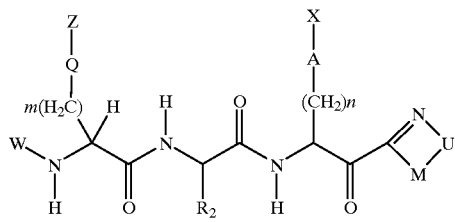

wherein:

m is 0, 1, 2, 3 or 4;

n is 3 or 4;

$R_2$ is H or $C_{1-3}$ alkyl;

A is absent;

M is O or S;

Q is piperdinyl, pyrrolidinyl, phenyl or is absent;

U is selected from the group consisting of

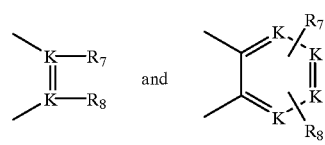

where n is 0–2; $R_7$ and $R_8$ are H; and K is C;

W is selected from the group consisting of aryl$C_{1-3}$alkylsulfonyl, arylsulfonyl, substituted arylsulfonyl, aryl$C_{1-4}$alkenylsulfonyl, $C_{1-8}$alkylsulfonyl, heteroaryl$C_{1-3}$alkylsulfonyl and heteroarylsulfonyl;

X is selected from the group consisting of NH—C(NR'R")=NH, NH—C(NHR')=NR— and NH—C(R')=NR"; where: R',R" are the same or different and are H or methyl;

Z is selected from the group consisting of NH—C(NR'R")=NH, NH—C(NHR')=NR", NH—C(R')=NR", C(NR'R")=NH and C(NHR')=NR";

where R'R" are the same or different and are H or methyl;

wherein said compound is a selective Factor Xa inhibitor and has an $IC_{50}$ of less than about 0.5 $\mu$M for Factor Xa;

or a pharmaceutically acceptable isomer, salt, hydrate, or solvate thereof.

40. The compound of claim 39 wherein U is

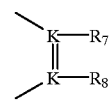

.

41. The compound of claim 39 wherein W is selected from the group consisting of aryl$C_{1-3}$alkylsulfonyl, aryl$C_{1-4}$alkenylsulfonyl, $C_{1-8}$alkylsulfonyl and heteroaryl$C_{1-3}$alkylsulfonyl.

42. The compound of claim 39 wherein R' and R" are H.

43. A method for treating a condition in a mammal characterized by undesired thrombosis comprising administering to said mammal a therapeutically effective amount of a compound of claim 1, 2, or 6.

44. The method of claim 43, wherein the condition is selected from the group consisting of:

acute coronary syndrome, myocardial infarction, unstable angina, refractory angina, occlusive coronary thrombus occurring post-thrombolytic therapy or post-coronary angioplasty, a thrombotically mediated cerebrovascular syndrome, embolic stroke, thrombotic stroke, transient ischemic attacks, venous thrombosis, deep venous thrombosis, pulmonary embolus, coagulopathy, disseminated intravascular coagulation, thrombotic thrombocytopenic purpura, thromboangiitis obliterans, thrombotic disease associated with heparin-induced thrombocytopenia, thrombotic complications associated with extracorporeal circulation, thrombotic complications associated with instrumentation such as cardiac or other intravascular catheterization, intra-aortic balloon pump, coronary stent or cardiac valve, and conditions requiring the fitting of prosthetic devices.

45. A method for inhibiting the coagulation in a biological sample, comprising contacting said sample with a compound of claims 1, 2 or 6.

\* \* \* \* \*